United States Patent
Naghavi et al.

(10) Patent No.: US 8,956,387 B2
(45) Date of Patent: Feb. 17, 2015

(54) SYSTEMS FOR REPLICATING THE BENEFICIAL EFFECTS OF PHYSICAL EXERCISE AND IMPROVING CARDIOVASCULAR HEALTH

(71) Applicant: ICT Therapeutics, Inc., Houston, TX (US)

(72) Inventors: Morteza Naghavi, Houston, TX (US); Albert Yen, Pearland, TX (US); Timothy O'Brien, Anoka, MN (US); Stephan Cleboski, Houston, TX (US); Timothy Brinkley, Sugar Land, TX (US); David Panthagani, Houston, TX (US)

(73) Assignee: IC Therapeutics Inc., Houston, TX (US)

( * ) Notice: Subject to any disclaimer, the term of this patent is extended or adjusted under 35 U.S.C. 154(b) by 0 days.

(21) Appl. No.: 14/104,225

(22) Filed: Dec. 12, 2013

(65) Prior Publication Data

US 2014/0114117 A1  Apr. 24, 2014

Related U.S. Application Data

(63) Continuation-in-part of application No. 12/323,392, filed on Nov. 25, 2008.

(51) Int. Cl.
| | | |
|---|---|---|
| *A61B 17/00* | (2006.01) | |
| *A61N 2/00* | (2006.01) | |
| *A61M 37/00* | (2006.01) | |
| *A61B 5/01* | (2006.01) | |

(Continued)

(52) U.S. Cl.
CPC .............. *A61N 2/002* (2013.01); *A61M 37/00* (2013.01); *A61B 5/01* (2013.01); *A61B 17/135* (2013.01); *A61B 17/1355* (2013.01); *A61B 5/14551* (2013.01); *A61B 5/02233* (2013.01); *A61B 5/417* (2013.01); *A61B 5/02225* (2013.01); *A61F 2007/0031* (2013.01); *A61N 1/0484* (2013.01); *A61N 1/36014* (2013.01); *A61N 1/0456* (2013.01); *A61N 1/0452* (2013.01); *A61N 1/36003* (2013.01)
USPC ......................................................... 606/201

(58) Field of Classification Search
CPC ............... A61B 17/135; A61B 17/132; A61B 17/1322; A61B 5/022; A61B 5/02225
USPC ................... 606/201–203; 600/483, 490–499
See application file for complete search history.

(56) References Cited

U.S. PATENT DOCUMENTS

| | | | |
|---|---|---|---|
| 2002/0103423 A1* | 8/2002 | Chin et al. | 600/322 |
| 2006/0167390 A1* | 7/2006 | Hui | 601/152 |

*Primary Examiner* — Thomas McEvoy
(74) *Attorney, Agent, or Firm* — David McEwing

(57) ABSTRACT

A system and method for inducing physiological effects of ischemic conditioning and physiological effects of shear stress in a subject's body that mimic the effect of exercise on the subject. The disclosure includes a first device configured to cause ischemia, a second device configured to mechanically generate arterial shear stress, and a third device configured to monitor one or more of markers of ischemia or hemodynamic parameters and further including a microcontroller and actuators to cause the ischemia for a preset duration and then stop the ischemia for a preset duration, and to repeat the ischemia and reflow periods according to a preset program, simultaneously cause the second device to mechanically generate arterial shear stress according to a preset program of mechanical pulse amplitude, duration, and frequency; and to concurrently monitor hemodynamic parameters or markers of ischemia. The method and device further includes application of electrical muscle stimulation, body vibration and chemical stimuli.

25 Claims, 19 Drawing Sheets

(51) Int. Cl.
*A61B 17/135* (2006.01)
*A61B 5/1455* (2006.01)
*A61B 5/022* (2006.01)
*A61B 5/00* (2006.01)
*A61F 7/00* (2006.01)
*A61N 1/04* (2006.01)
*A61N 1/36* (2006.01)

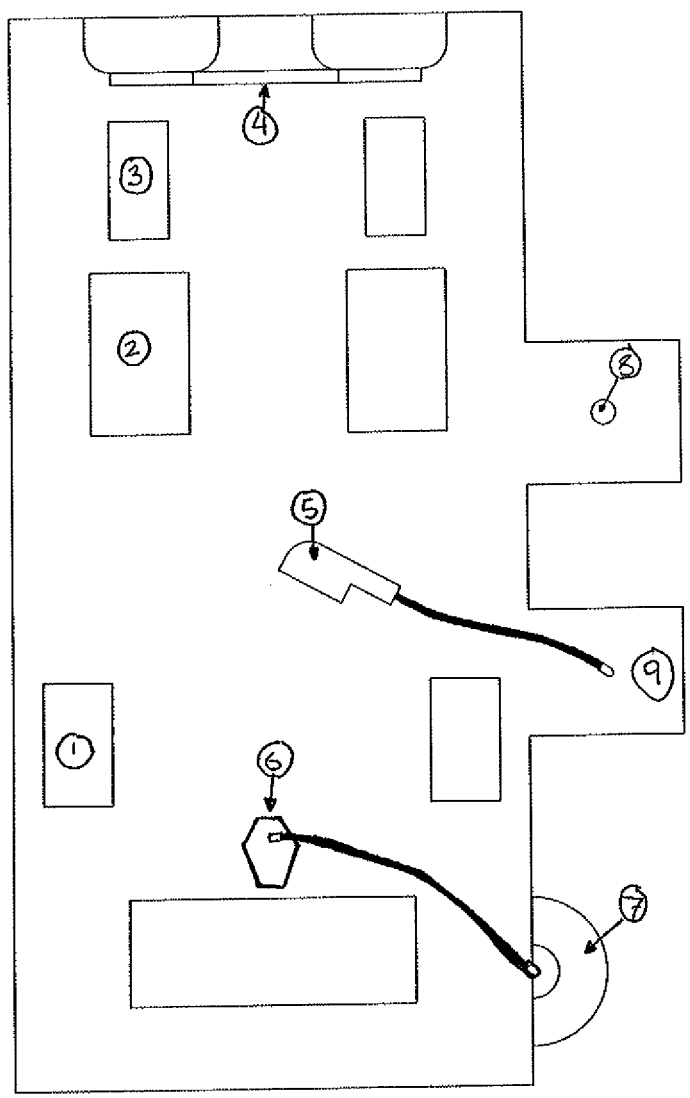

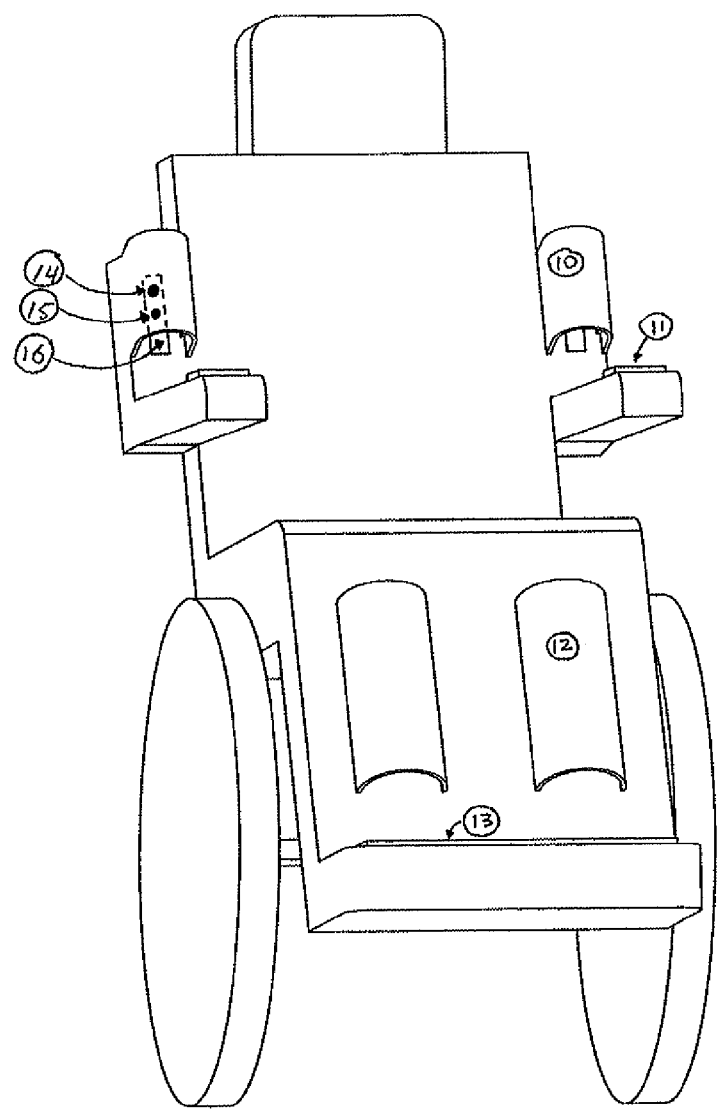

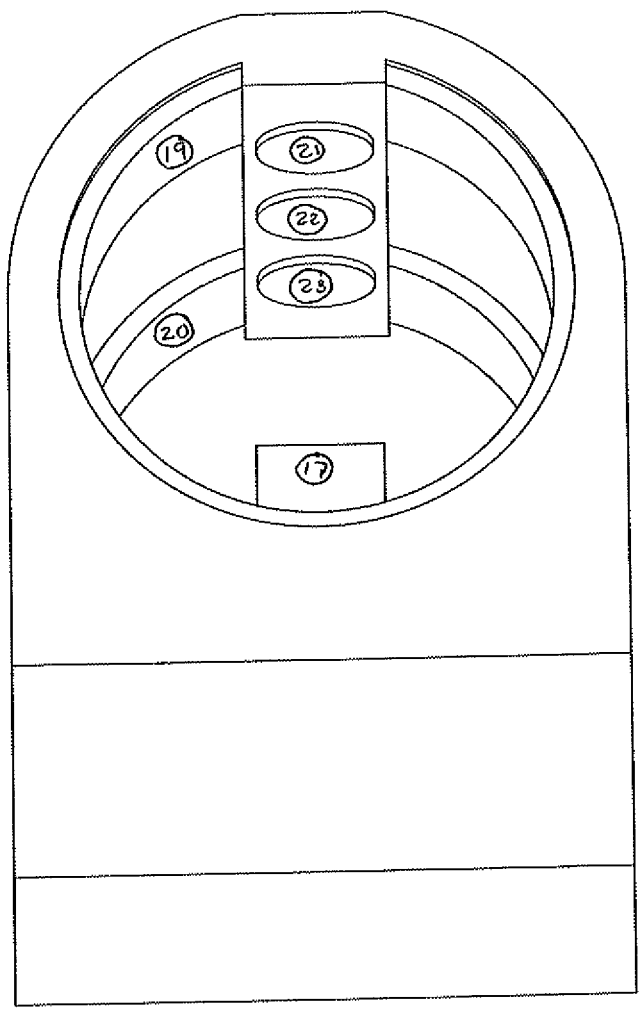

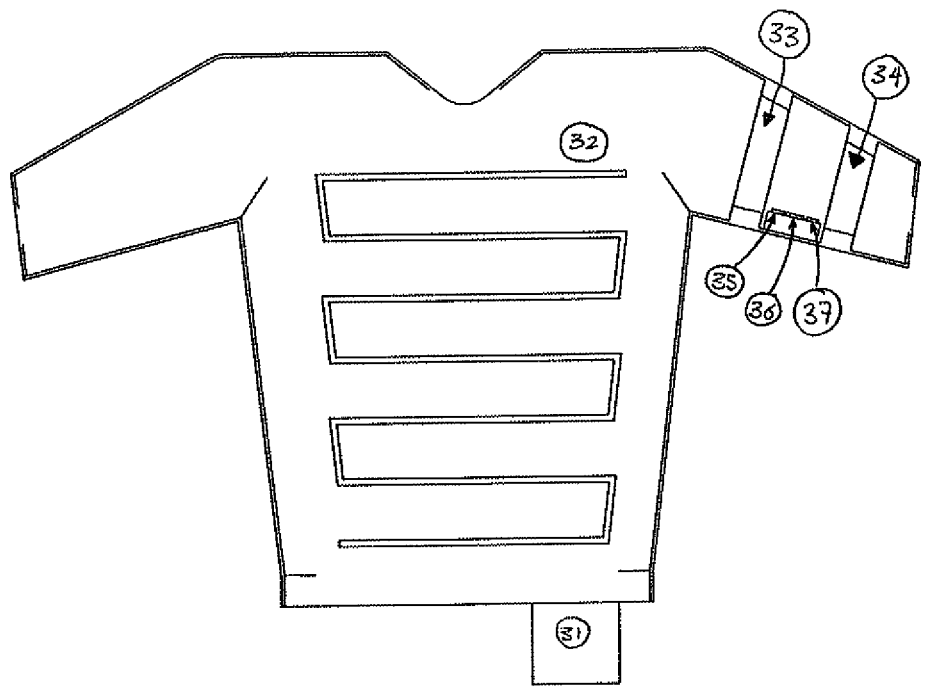

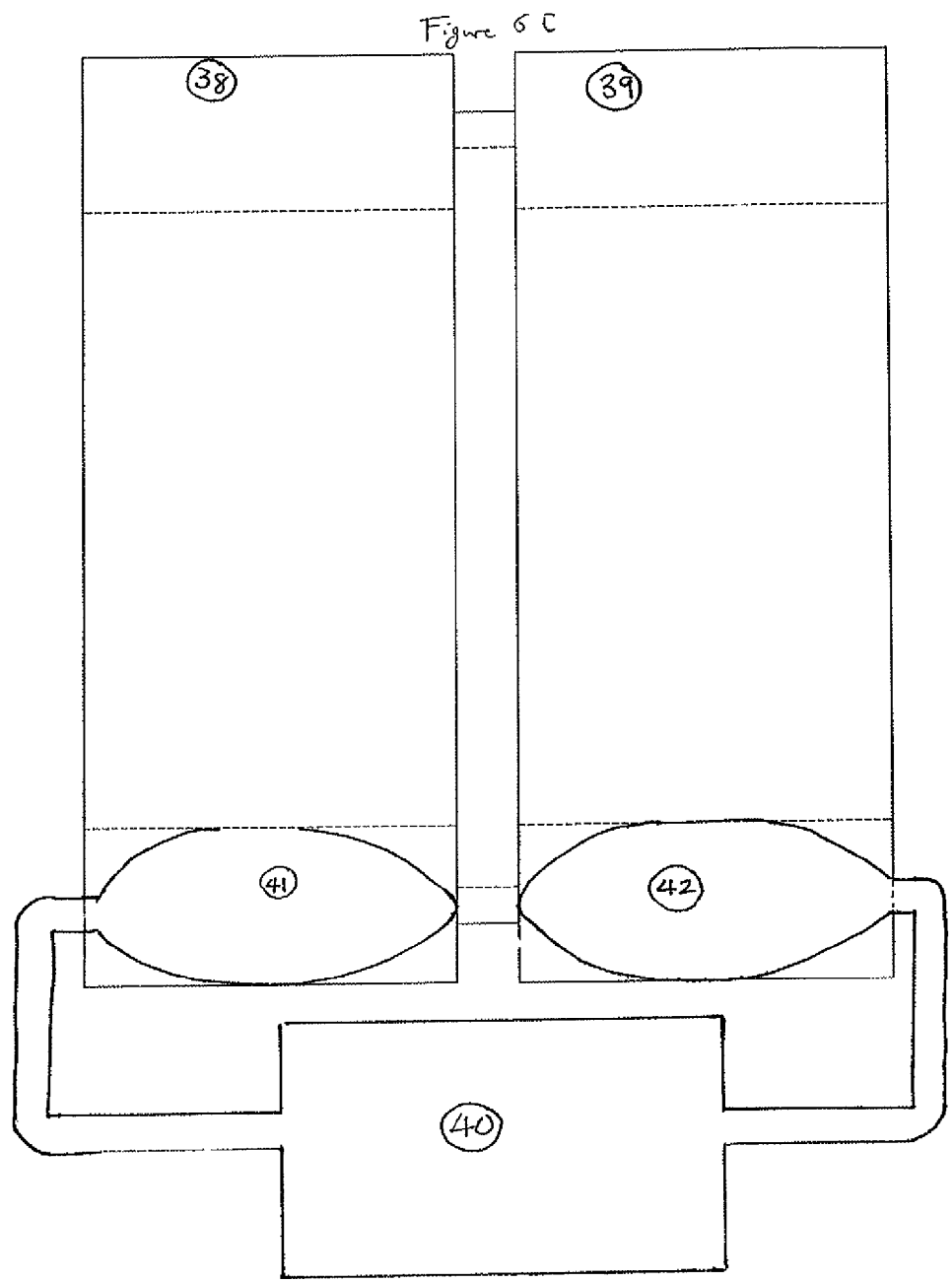

SYSTEMS FOR REPLICATING THE BENEFICIAL EFFECTS OF PHYSICAL EXERCISE AND IMPROVING CARDIOVASCULAR HEALTH

CROSS REFERENCE TO RELATED APPLICATIONS

This application is a Continuation In Part of application Ser. No. 12/323,392 filed Nov. 25, 2008 entitled "Methods and Apparatus for Repeated Ischemic Conditioning Treatment of Hypertension and Similar Conditions" which is incorporated by reference in its entirety herein. This application claims priority based on U.S. Provisional Application No. 60/989,946 filed Nov. 25, 2007, the disclosure of which is incorporated herein by reference in its entirety.

FIELD OF THE INVENTION

The present invention relates generally to the field of improving a person's cardiovascular health by a program replicating the beneficial physiological effects of exercise within a subject otherwise unsuited, unwilling, or physically unable to perform exercise functions. This invention improves the subject's health by, for example, creating ischemic conditions, increased blood shear stress by pulsation of blood, electrical muscular contraction, inducing vibration of tissue generating arterial shear stress and stimulating increases in bone density, and changes in blood chemistry, all in a manner collectively achieved only through physical exercise. The invention also creates enhanced physiological effects in athletes beyond those achievable in physical exercise.

BACKGROUND

The health benefits of regular physical exercise are well known. The benefits include but are not limited to improved cardiovascular health. However, motivation to engage is such a program is frequently lacking in a sizable percentage of the population. Pharmacological or drug therapies, e.g., statins, have been shown to marginally improve cardiovascular health. However, there may be detrimental side effects. Further, such drug regimens have been shown less effective than regular exercise. Further, it is known that cardiovascular disease may be caused and/or enhanced by an impairment of tissue perfusion. Cardiovascular health is a function of the health of the endothelium. The endothelium is directly benefited by devices and method taught by this disclosure.

However, even other noninvasive lifestyle approaches to chronic disease management can be tempered with side effects and ineffectiveness. For example, regular exercise is known to lower blood pressure in healthy individuals by inducing ischemia. Inducing ischemia by exercise may, however, also be problematic because it causes an increase in heart rate that may not be tolerated well by some individuals. Further, exercise, diet, and weight loss programs are all well known to suffer problems of compliance.

The endothelium has many important functions in maintaining the patency and integrity of the arterial system. The endothelium can reduce and inactivate toxic super-oxides which may be present in diabetics and in smokers. The endothelium is the source of nitric oxide, a local hormone that relaxes the adjacent smooth muscle cells in the media, and is a powerful vasodilator.

The endothelium regulates vascular homeostasis by elaborating a variety of paracrine factors that act locally in the blood vessel wall and lumen. Under normal conditions, these aspects of the endothelium, hereinafter referred to as "endothelial factors", maintain normal vascular tone, blood fluidity, and limit vascular inflammation and smooth muscle cell proliferation.

Arm cuff inflation provides a suprasystolic pressure stimulus. Ischemia reduces distal resistance and opening the cuff induces stretch in the artery. Imaging of the diameter of the artery with high resolution ultrasound along with measuring the peak flow defines endothelial function. However, this method requires very sophisticated equipment and operators that are only available in a few specialized laboratories worldwide.

A separate therapy for cardiovascular health is enhanced external counterpulsation therapy. This therapy requires monitoring and coordination with the cycle of the heartbeat. This therapy involves the propulsion of blood into the subject's torso during the diastole phase of the cycle. The movement of blood increases the shear stress on the arterial walls including endothelium. This is equivalent to the high shear stress achieved during exercise. This event is beneficial to the endothelium.

What is needed is a non-invasive and inexpensive physical conditioning treatment therapy or combination of therapies that reproduce or enhance the physiological effects of exercise.

SUMMARY OF DISCLOSURE

The disclosures herein relate generally to cardiovascular health and neurovascular conditions and more particularly to a method and apparatus for improving health conditions. In an embodiment, endothelial function may be improved by providing a vasodilating stimulant to a subject to stimulate hemodynamic activity in a selected region of the subject's body and simultaneously providing arterial shear stress in the subject's body. The arterial shear stress may be induced by mechanical vibration of all or part of a subject's body. It may also be created by mechanically creating performing a program of pulsating the arterial blood of a subject. In an embodiment, the subject experiences electrical stimulation of nerves and muscle groups producing muscle contractions and the release of biochemical markers associated with physical exercise without placing strain upon the subject's body and musculoskeletal system. In a further embodiment of the methods and apparatus taught by the disclosure, a chemical stimulator acts as an aid to create physiological effects of exercise and improve cardiovascular conditioning and performance. Examples are hypobaric chamber with low oxygen, administration of nitric oxide by inhalation, and administration of dobutamine and/or other sympathomimetic agents by intravenous, intramuscular, or subcutaneous routes. Also sympathomimetic drugs like dobutamine are used for increasing heart rate in cardiac nuclear imaging stress tests instead of bicycle/treadmill stress tests.

These effects create the physiological signature of exercise. As indicated, the disclosure also combines a method and device for creating involuntary contraction of at least one muscle group, thereby prompting the utilization of intracellular energy stores and the burning of calories. The device may be an electro-muscular stimulator. If placed on the subject's skin surface proximate to a peripheral nerve controlling a muscle group, repeating neural stimulation will trigger muscle contractions and mimic the effect of exercise, including the production of endorphins within the subject, as in the known technique of motor level electroanalgesia. The production of endorphins and consumption of calories further mimics the effects of exercise.

In one embodiment, ischemic conditioning is affected by transiently and repeatedly administering transient ischemia to at least one vascular area of a subject or part thereof. It has been shown that ischemia induced in one part of the subject's body beneficially affects the whole body. Ischemia may be induced in an area of the subject's body remote from the area of interest.

In an embodiment, a device for ischemic conditioning is provided. In one embodiment the device has one or more occluding components in addition to a controlling component. The controlling component may be programmable and the device may further include data storage components. A sensor for monitoring of tissue markers may be additionally provided. The capability of monitoring may communicate or be part of the controlling component. The occluding member may be adapted to at least partially occlude an internal vascular lumen to reduce or occlude flow to at least one peripheral tissue of the subject. In another embodiment, the device can occlude an artery such as the brachial artery of an arm, femoral artery in the subject's thigh or tibial artery in the subject's lower leg. In an embodiment, external skin pressure is provided to induce ischemia only at the skin and/or subdermal levels.

The programmable controlling member (e.g., a microcontroller) may be adapted to control the frequency and duration of ischemia in a tissue according to an ischemic conditioning protocol. It also can control the duration of reperfusion. In an embodiment, an occluding or constricting member is controlled by a separate programmable device. In an embodiment, the occluding or constricting member may be an inflatable cuff or non-invasive electrical stimulator. The programmable member can include a data storage member, such as a computer or microprocessor, and may be adapted to store the protocol and/or monitoring results. Alternatively, the programmable member may be a microcontroller, including a CPU, RAM, ROM, and I/O ports, built within it. For purposes of this disclosure, computer, CPU, microprocessor and microcontroller will be referred to as "microcontroller". An optional display may be provided to show the ischemic conditioning protocol, stored data, results of the ischemic conditioning, and/or other relevant data. The devices described herein may be adapted for home or clinical use. For example, a device for home use may simply utilize external cuff occlusions around an extremity, blood pressure measurement, temperature and/or pulse monitoring.

In further embodiments, the ischemia of the tissue distal to the occlusion site is monitored by a temperature sensor and/or an artificial pulse oximetry sensor. For reasons described more fully below, the digit containing a temperature sensor or artificial pulse oximetry sensor may be isolated or insulated to preclude contact with other portions of the subject's body or other heat source.

In other embodiments, the device for inducing ischemic conditioning includes an occluding member (which may be referenced as "the first occluding device") adapted to occlude an artery and cause ischemia, a programmable controlling member (microcontroller) adapted to control frequency and duration of ischemia in a tissue based on measuring blood pressure and which may be adapted to use oscillometric signals to maintain suprasystolic occlusion pressure, and a temperature or pulse oximetry monitor of ischemia in the tissue. The temperature may be measured from the skin surface.

In one embodiment of the invention, repeated ischemic conditioning is applied to confer pharmacologic-like and exercise-like therapeutic effects by increasing the vasodilative capacity of the vasculature in the limbs in order to positively affect a vascular condition.

The beneficial effects of the ischemic conditioning treatment are not limited to the treated extremity but rather experienced by all parts of the subject's body, including internal organs. Therefore, the site in which ischemia is induced may be remote from the portion of the subject's body of interest.

In one embodiment, ischemic conditioning is elicited by transiently and repeatedly administering the treatment to at least one limb, or part thereof, for inducing the physiological effects of exercise. The ischemic conditioning treatment in one embodiment is transiently and repeatedly applied according to a schedule that is tailored to the medical and psychosocial needs of the individual subject. In accordance with one embodiment, the program of ischemic conditioning includes at least 1 cycle of from 1 to 20 minutes of occlusion on at least one extremity, at least 2-4 times per week. In one embodiment, the program of ischemic conditioning includes at least 1 cycle of from about 2 to about 5 minutes of occlusion. The program can be adapted to the subject by monitoring the relationship between different administration protocols and the blood pressure of the subject with a goal of replicating the effects of physiologic effects of exercise, including but not limited to decrease levels of oxygen, increased levels of carbon dioxide, increased levels of nitric oxide, etc. The monitored hemodynamic markers of the disclosure are to monitor one or more of markers of ischemia or hemodynamic parameters such as tissue oxygenation and temperature; markers of metabolism including lactate, pH, oxygen, carbon dioxide, ATP, ADP, adenosine, cytochrome oxidase, redox voltage, erythropoietin, bradykinin, opioids; and markers of blood flow or pulse; or combinations thereof.

In one version of the invention, the program of ischemic conditioning includes at least 2 cycles of about 2 to about 5 minutes of occlusion followed by about 2 to about 5 minutes of release of an extremity at least 2-4 times per week.

In one embodiment of the invention, the ischemic conditioning is applied to one or more extremities using an external cuff system for arterial occlusion. In another embodiment, the occlusion is created by a clamp like device place over the brachial or femoral artery. Alternatively or in addition, the ischemic conditioning is applied to one or more extremities using external pressure to the skin using a pressurizable garment.

In other embodiments, the ischemic conditioning includes a measurement aspect comprising one or more of determining a digital temperature monitor (DTM response) and a determination of blood oxygen saturation during ischemia using artificial pulse together with oximetry to improve the ischemic conditioning treatments. The artificial pulse may be generated by mechanical actuation. In some version of the invention, the mechanical actuation is affected by pulsating fluid pressure in a cuff to cause mechanical disturbance of arterial blood, repetitive, external electromechanical actuation, or repetitive, self-induced physical motion. Alternatively or in addition, the artificial pulse may be generated by external non-mechanical optical illumination utilized to imitate an absorption pattern of a pulsatile blood flow signal by oscillating an intensity of a light source of either a single or multiple wave length. Assessment of the progress of the ischemic conditioning treatment may include measuring one or more baseline hemodynamic parameters of a subject, applying an ischemic conditioning treatment in the subject by occluding and releasing arterial flow in one or more extremities of the subject on a scheduled, repeated basis, measuring post-ischemia parameters in the subject, and comparing the baseline and post-ischemia parameters to provide an assessment of the ischemic conditioning treatment over time.

In one embodiment, an apparatus is provided for transiently inducing ischemia in a peripheral vascular area of a subject, the apparatus including a plurality of releasable compressing elements, each adapted to reduce or occlude flow of blood to at least a portion of an extremity of the subject. The releasable compressing elements may comprise bands dimensioned to be tightened around at least one extremity such as an arm and/or leg to occlude flow of blood to at least a portion of the hands and/or feet. Alternatively, the releasable compressing elements may comprise inflatable compression suits, mittens, socks, stockings, gloves and/or full body suits.

In one embodiment of the invention, apparatus for transiently and repeatedly inducing ischemia in a peripheral vascular area of a subject includes use of a plurality of releasable bands or clamp-like devices, each adapted to occlude blood supply to at least a hand or foot of the subject when tightened or inflated. As used here, the term band includes cuffs such as inflatable blood pressure type cuffs.

The clamp devices can consist of a plunger system to occlude a target artery such as the brachial artery of the arm or the femoral artery in the leg. Considering the clamp system used to occlude the brachial artery, the system uses a plunger to occlude an artery using a screw device. Other methods are contemplated by this disclosure such as pistons, rack and pinion or automated systems using servo motors or stepper motors. The brachial artery can be used as the artery for occlusion. Occlusion can occur at the cubital fossa rather than at the bicep level of the subject's arm.

This clamp device and method also uses a feedback system that incorporates a pressure or force transducer to detect the amount of force so that the force exerted can be regulated either manually by the user or automatically by the device. The force transducer can be located at the focal point of the clamp contacting the subject's skin. This allows the amount of force on the arm to be minimized. It also allows for continual reassessment of the force applied.

The device may use a padded cup shaped device placed proximate to the elbow and opposite the position of an occlusion plunger. The occlusion plunger moves against the skin surface to exert pressure on the subcutaneous artery. The device uses either motorized or a hand-powered system to drive the occlusion plunger toward the arm. A force or pressure transducer is used to detect the amount of force so that the force exerted can be regulated either manually by the user or automatically by the device. As an option, the device has an emergency release system that causes the device to separate or open on a hinge system so that the subject's limb can be removed immediately if the need arises.

The apparatus may be manual in operation or may be automated such as with a control device for controlling inflation/compression and release of elements in accordance with a schedule. In one embodiment the apparatus includes a programmable computer, CPU, microprocessor or similar control device (hereinafter "microcontroller") for inducing ischemia in accordance with a schedule. In one embodiment the apparatus further includes a pump in operable communication with the releasable compressing elements, wherein the action of the pump results in tightening or inflation by filling of the releasable compressing elements, e.g., fluid such as air.

In a further embodiment of the invention, the device may comprise a second cuff or at least partially occluding device position distally from the first occluding device. This device, termed a vasculature stress conditioner, can be programmed to partially compress the occluded artery at two to five second intervals to create movement of blood within the occluded artery and companion venous system. This movement induces shear stress on the endothelium lining of the lumens. This shear stress further mimics the effects of exercise. For example, it has been shown that induced shear stress induces production of NO within the endothelium. This causes dilation of the lumen, a phenomena experienced during exercise.

It has been shown that enhanced external counterpulsation (EECP) can benefit subjects with coronary artery disease (CAD). Enhanced external counterpulsation enhances peripheral endothelial function with beneficial effects persisting at one-month follow-up in patients with a positive clinical response. This suggests that improvement in endothelial function may contribute to the clinical benefit of EECP in patients with symptomatic CAD. One of the mechanisms by which EECP may exert its clinical benefit is by increasing exercise capacity. EECP provides hemodynamic stimuli similar to those of physical exercise that contribute to the improvement in endothelial function. In line with this concept are the results of studies showing an enhancement of exercise tolerance, whereas peak exercise double product is maintained due to a decrease in maximal blood pressure in some patients after a course of EECP. These results indicate that EECP, similar to physical training, promotes an exercise induced decrease in peripheral vascular resistance. Given the importance of endothelial function for the regulation of vascular tone and peripheral vascular resistance, the results support the notion of the existence of such a peripheral "training" effect of EECP. See *Enhanced External Counterpulsation Improves Endothelial Function In Patients With Symptomatic Coronary Artery Disease*, Journal of the American College of Cardiology Vol. 41, No. 10, 2003, © 2003 by the American College of Cardiology Foundation, Published by Elsevier Inc Shear stress also liberates prostacyclin from endothelium and relaxes vascular smooth muscle as an endothelium independent vasodilator. In most blood vessels, the contribution of prostacyclin to endothelial-dependent vasodilation is small and its effect is additive to nitric oxide. However, in terms of preventing platelet aggregation, leukocyte adhesion to endothelium, and susceptibility to thrombosis, the action of prostacyclin and nitric oxide are synergistic. Nitric oxide has an inhibitory effect on prostacyclin production under shear stress but vessel homeostasis is maintained through an increase in prostacyclin production.

In one embodiment the first occluding cuff can be part of the same structure of the second partially compressing cuff. Again, the first cuff is used to create the occlusion. The second cuff is used to pulsate the blood in the subject's limb. In one embodiment, the second partially occluding cuff is placed distally from the first occluding cuff. In another embodiment, the partially occluding cuff can be placed proximately to the occluding cuff. As explained in greater detail herein, the second partially occluding cuff pulsates the subject's blood. The inflation stage may be shorter than the inflation of the occluding cuff. There may be more cycles of inflation/deflation of the second cuff. It will also be appreciated that the first cuff may be programmed to only partially occlude the subject's artery. The first cuff may not be required to achieve greater than systolic pressure.

This dilative effect (vasculature shear stress conditioning) can also be produced within the subject by placing separate inflatable cuffs on preferably the lower extremities of the subject and synchronizing the inflation of these cuffs with the systolic/diastolic rhythm of the heart beat. In one embodiment, a plurality of cuffs arranged distal to proximal on the extremity can be sequentially inflated during the diastolic phase of the heart beat to create a retro flow through the subject's torso. This flow creates a shear stress on the arteries of the subject's torso during the otherwise resting phase of the heart beat. An electrocardiogram machine can be used in conjunction with the device microcontroller to coordinate the occlusion of the device with heart beat rhythm.

In yet a further embodiment, electro-muscular stimulating devices can be placed on selected locations of the subject's skin surface. The electro-muscular simulating devices may be placed proximate to one or more muscle groups of the subject. Even more preferred is placing the electro-muscular stimulating devices proximate to a peripheral nerve of the subject's body. In one embodiment, the electro-muscular stimulating device may be part of the structure of an inflatable or clamp device.

In yet another embodiment, the disclosure may be practiced with devices causing vibration within the subject. This is practiced simultaneously with ischemic conditioning therapy and vasculature shear conditioning above. Vibration can induce arterial shear stress in the subject, production of nitric oxide and to stimulate bone density growth, etc. Disclosed is use of devices vibrating at less than 80 Hz. Preferably the device vibrates at less than 30 Hz. The vibration is induced within the subject by placement of an external vibrating surface onto the skin of the subject. The device can utilize, for example, a servo-motor. The device can be controlled by the user through the microcontroller.

An embodiment can simultaneously use a chemical stimulator as an aid to create physiological effects of exercise. For example, a hypobaric chamber or low oxygen high $CO_2$ ventilation, inhaling NO, or sympathomimetic drugs like dobutamine (that are used for increasing heart rate in cardiac nuclear imaging stress tests instead of bicycle/treadmill stress tests) can be used. In an embodiment, the chemical stimulator may be used 1 to 20 minutes before the ischemic conditioning therapy. Dispersement of the chemical stimulator can be controlled through the microcontroller.

In another embodiment, the disclosure teaches a device that can be used in support or enhancement of treatment utilizing a left ventricular assist device (LVAD). It will be appreciated that LVAD's preferably create a continuous stream of oxygen enriched blood into the aortic system. Without being limited to theory, this mode of operation avoids the creation of blood clots. However this mode of operation sacrifices the beneficial effects created by the shear stress of a pulsating blood flow. An embodiment of the disclosure can provide a source of pulsating blood by the cyclic inflation and deflation of a cuff or a plurality of sequenced cuffs. Therefore the subject, treated with an LVAD, can experience the physiological effects of a pulsating blood supply. This effect occurs in conjunction with ischemic conditioning therapy. It may also be combined with electrical muscle stimulation and chemical stimulation therapy.

BRIEF DESCRIPTION OF THE DRAWINGS

The accompanying drawings, which are incorporated in and constitute a part of the specification, illustrate preferred embodiments of the invention. These drawings, together with the general description of the invention given above and the detailed description of the preferred embodiments given below, serve to explain the principles of the invention.

FIG. 1B illustrates a top view of the treatment bed showing the tank containing therapeutic gas and mask for subject. Also shown are the components holding inflatable cuffs for the subject's arms, thighs, and lower legs. Also shown is a vibration plate 4 upon which the subject's feet may be placed during treatment. Also illustrated is an IV pole 8 from which therapeutic medication can be hung. Also shown is the controller 5, 9.

FIG. 2A illustrates a schematic view of a chair comprising a component comprising an inflatable cuff 10 and a vibration plate 11 on the arm or hand rest. Also shown are components for inflation cuffs 12 for the lower legs and a vibration plate 13 on the chair footrest. Also illustrated is a heating element 14. The heating element applies therapeutic levels of heat to the subject. The duration of heating and the temperature are determined by a microcontroller. Also illustrated is a muscle stimulation electrode 15, and an upper arm vibration plate 16.

FIG. 3C illustrates a back view of the device showing the pulsatile cuff 20, the upper arm heating element 21, the upper arm muscle stimulation electrode 22 and the upper arm vibration plate 23. The upper arm muscle stimulation electrode applies small amounts of current for therapeutic transcutaneous muscle stimulation. The amount of current, duration, and frequency of application are determined by a microcontroller. Number 23 shows the Upper Arm Vibration Plate. The subject's arms pressed against these plates to transmit therapeutic vibrations ranging from 3-50 Hz. The frequency and amplitude of the vibration are determined by a microcontroller.

FIG. 5B illustrates a further back view of the showing the control interface 31, the garment back and heating element 32. Also shown is the upper arm heating element 35, the upper arm muscle stimulation electrode 36 and the upper arm vibration plate 37. Also shown are the ICT cuff 33 and the pulsatile cuff 34.

FIGS. 6A, 6B and 6C illustrate a combined cuff. The combined cuff device contains two separate bladders 41, 42.

DETAILED DESCRIPTION

Figure 1A:
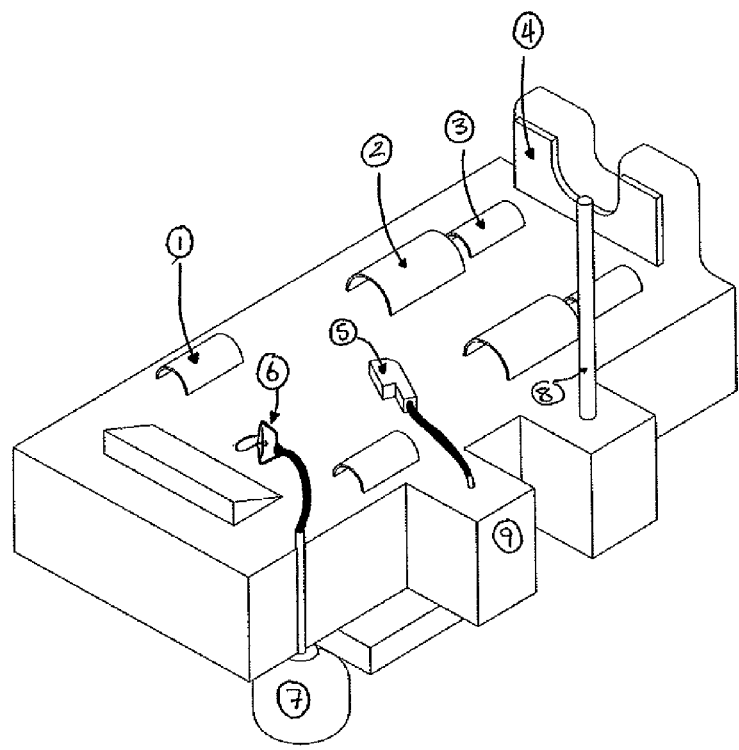
FIG. 1A illustrates a schematic view of a bed teaching ischemic conditioning, vasculature shear stress conditioning, vibration conditioning and chemical therapy. The bed includes a cuff 1 placed over the subject's arm and cuffs 2, 3 that can be placed over the subjects upper and lower leg. Also shown is a mask 6 that can be used by the subject to receive a chemical stimulant and the related storage tank 7.

The method and device of this disclosure pertains to inducing physical effects within a subject similar to the effects achieved through physical exercise. In one embodiment, the induced effects surpass or enhance the effects of normal exercise. In this manner, it may be used for athletic training. In another embodiment, it may be used to produce physiological effects in subject's otherwise unable to tolerate or is unwilling to perform physical exercise. This can include subjects suffering from coronary artery disease, heart failure, stroke, spinal cord injury or any subject that is confined to a bed or chair.

One method, termed ischemic conditioning therapy (ICT), is combined with other therapeutic techniques to produced superior or enhanced physiological effects on a subject. These other therapies include vascular shear conditioning (comprising induced pulsations in arterial and venous blood), electrical muscle stimulation (which may be either neural or muscular stimulation), use of chemical stimulators such as inhaling nitric oxide or administering sympathomimetic agents, and use of vibration whole or partial body stimulation.

As used herein the term "ischemia" means lowering of baseline blood flow to a tissue. The term "hypoxia" means lowering of arterial $PO_2$. Both ischemia and hypoxia in extremities can be induced by occluding the blood supply upstream of the extremity. By "extremity" it is meant the limbs (arms and legs). By "distal extremity" it is meant the hands and feet, including the digits of the hands and feet. By "proximal" it is meant the region closer to the heart. By "distal" it is meant to be a region more distant from the heart. By "regional or local" it is meant, administration to a defined area of the body as contrasted with systemic administration. One embodiment of the present invention employs transient, intermittent ischemia to condition and improve the vasculature of the extremities.

As used herein the phrase "compounds that increase the bioavailability of nitric oxide (NO)" include NO precursors, NO donors and NO agonists. An example of a NO precursor is the essential amino acid substrate L-arginine from which NO is synthesized by the action of nitric oxide synthase (NOS). NO donors, which generate NO via NOS independent processes, include both fast and slow release compounds that typically release NO by either oxidation or reduction. Certain of the NO donor compounds such as nitroglycerin (an organic nitrate), which is enzymatically degraded to generate NO, have been utilized for over a century. Examples of NO donors (sometimes alternatively referred to in art as NO agonists) include the organic nitrates (e.g. glyceryl trinitrate, isosorbide dinitrate), sodium nitroprusside (SNP), syndnonimines (e.g. molsidomine, SIN-1), S-nitrosothiols (e.g. s-nitrosoglutathione), NONOates (e.g. Spermine-NONOate, DETA-NONOate), and hybrid donors such as the nitroaspirins and nicorandil. Certain other compounds that are considered herein to fall within the definition of compounds that increase the bioavailability of NO are compounds, and metabolites thereof, that include nitric oxide chemical structures and are considered to be NO agonists such as for example minoxidil (3-hydroxy-2-imino-6-(1-piperidyl)pyrimidin-4-amine). Such compounds are considered herein to be NO agonists if their action is the same as NO, such as for example, in opening of membrane potassium channels.

Considering now the drawings accompanying this disclosure, FIG. 1A illustrates and ICT arm cuff 1. This is a pneumatic arm cuff capable of measuring blood pressure and inflating to suprasystolic pressure for ICT treatments. The cuff is also capable of pulsatile inflation where the pulse frequency, duration and pressure are determined by a microcontroller. Also illustrated is an upper leg cuff 2. This pneumatic leg cuff can inflate to suprasystolic pressure for ICT treatments. The cuff is also capable of pulsatile inflation where the pulse frequency, duration, and pressure are determined by a microcontroller. Number 3 shows a Lower Leg Cuff. This pneumatic leg cuff that can inflate to suprasystolic pressure for ICT treatments. The cuff is also capable of pulsatile inflation where the pulse frequency, duration, and pressure are determined by a microcontroller. Also illustrated is a foot vibration plate 4. The subject's feet are pressed against this plate to transmit therapeutic vibrations ranging from 3-50 Hz. The frequency and amplitude of the vibration are determined by a microcontroller. FIG. 1A also illustrates an ultrasound transducer 5. The ultrasound transducer is connected to the ultrasound generator 9 to apply therapeutic ultrasound treatment to the subject. Also shown is a mask 6 that attaches to the subject's face and allows for inhalation of gaseous chemical stimuli. The mask is connected to a holding tank 7 where a gaseous chemical stimulus is stored. The rate of gas release into the face mask, the pressure, and the temperature is maintained by a microcontroller. Also shown is the intravenous apparatus (IV) apparatus 8. The IV apparatus is used to hang IV drips. Also shown is the ultrasound generator 9. The generator creates therapeutic ultrasound and is applied using the ultrasound transducer.

FIG. 1B illustrates a top view of the bed.

Figure 2B:
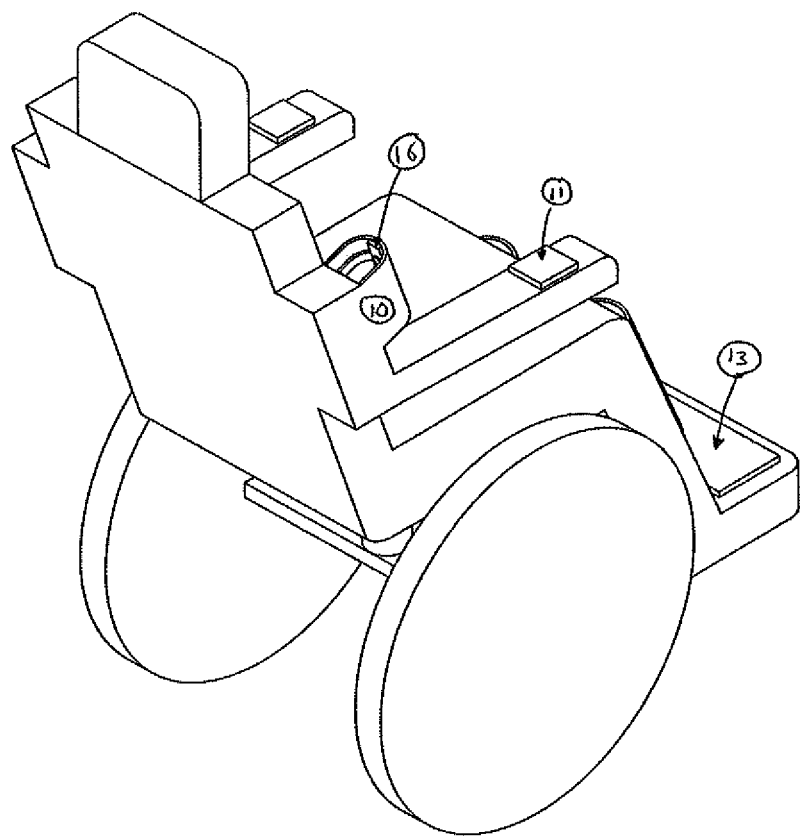
FIG. 2B illustrates another schematic view of the chair.

FIGS. 2A and 2B show a chair/wheelchair configuration. Illustrated is an ICT Arm Cuff 10. This is a pneumatic arm cuff capable of measuring blood pressure and inflating to suprasystolic pressure for ICT treatments. The cuff is also capable of pulsatile inflation where the pulse frequency, duration, and pressure are determined by a microcontroller. Also shown is a hand vibration plate 11. The subject's hands are pressed against this plate to transmit therapeutic vibrations ranging from 3-50 Hz. The frequency and amplitude of the vibration are determined by a microcontroller. Also shown is a lower leg cuff 12. This pneumatic leg cuff that can inflate to suprasystolic pressure for ICT treatments. The cuff is also capable of pulsatile inflation where the pulse frequency, duration, and pressure are determined by a microcontroller. A foot vibration plate 13 is also shown. The subject's feet are pressed against this plate to transmit therapeutic vibrations ranging from 3-50 Hz. The frequency and amplitude of the vibration are determined by a microcontroller. A heating element is also shown 14. The heating element applies therapeutic levels of heat to the subject. The duration of heating and the temperature are determined by a microcontroller. Shown is a muscle stimulation electrode 15. The electrode applies small amounts of current for therapeutic transcutaneous muscle stimulation. The amount of current, duration, and frequency of application are determined by a microcontroller. These variables can be programmed into the microcontroller. The settings can be modified for each individual subject. An upper arm vibration plate is also shown 16. The subject's arms pressed against these plates to transmit therapeutic vibrations ranging from 3-50 Hz. The frequency and amplitude of the vibration are determined by a microcontroller.

FIGS. 3A, 3B, 3C and 3D illustrate an arm unit for therapeutic treatment. Shown is hand vibration bar 17. The bar is gripped in the subjects hand to transmit therapeutic vibrations ranging from 3-50 Hz. The frequency and amplitude of the vibration are determined by a microcontroller. A forearm heating element 18 is also shown. The heating element applies therapeutic levels of heat to the subject. The duration of heating and the temperature are determined by a microcontroller.

An ICT occlusion cuff 19 is also shown. This is a pneumatic arm cuff capable of measuring blood pressure and inflating to suprasystolic pressure for ICT treatments. The pressure, duration, and number of cycles for ICT are determined by a microcontroller.

Also shown is the pulsatile cuff 20. This is a pneumatic arm cuff capable of measuring blood pressure and inflating in pulses before, during, or after ICT treatments. The pressure, duration, and frequency for the pulses are determined by a microcontroller. Also shown is the upper arm heating element 21. The heating element applies therapeutic levels of heat to the subject. The duration of heating and the temperature are determined by a microcontroller. Also shown is the upper arm muscle stimulation electrode 22. The electrode applies small amounts of current for therapeutic transcutaneous muscle stimulation. The amount of current, duration, and frequency of application are determined by a microcontroller. Lastly, FIGS. 3A, B, C, and D shows the upper arm vibration plate 23. The subject's arms pressed against these plates to transmit therapeutic vibrations ranging from 3-50 Hz. The frequency and amplitude of the vibration are determined by a microcontroller.

Figure 4:
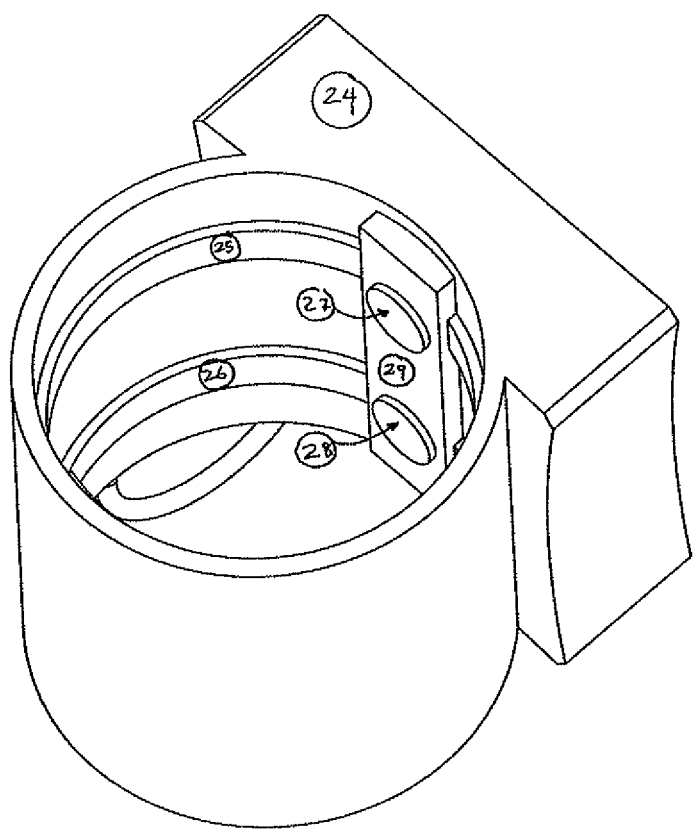
FIG. 4 illustrates a portable arm treatment device showing a user interface and microcontroller 24 and an ICT occlusion cuff 25. Also shown is a pulsatile cuff 26, and upper arm heating element 27 and an upper arm muscle stimulant component 28.

FIG. 4 illustrates a portable arm unit. Illustrated is the user interface and microcontroller 24. The microcontroller is responsible for user input and controlling the various functions of the device and contains battery for portable use. The ICT occlusion cuff 25 is also illustrated. This is a pneumatic arm cuff capable of measuring blood pressure and inflating to suprasystolic pressure for ICT treatments. The pressure, duration, and number of cycles for ICT are determined by a microcontroller 24. The pulsatile cuff 26 is illustrated. This is a pneumatic arm cuff capable of measuring blood pressure and inflating in pulses before, during, or after ICT treatments. The pressure, duration, and frequency for the pulses are determined by a microcontroller 24.

FIG. 4 also shows the upper arm heating element 27. The heating element applies therapeutic levels of heat to the subject. The duration of heating and the temperature are determined by a microcontroller 24. Number 28 shows the upper arm muscle stimulation electrode. The electrode applies small amounts of current for therapeutic transcutaneous muscle stimulation. The amount of current, duration, and frequency of application are determined by the microcontroller 24. Finally an upper arm vibration plate 29 is illustrated. The subject's arm is pressed against this plate to transmit therapeutic vibrations ranging from 3-50 Hz. The frequency and amplitude of the vibration are determined by a microcontroller 24.

Figure 5A:
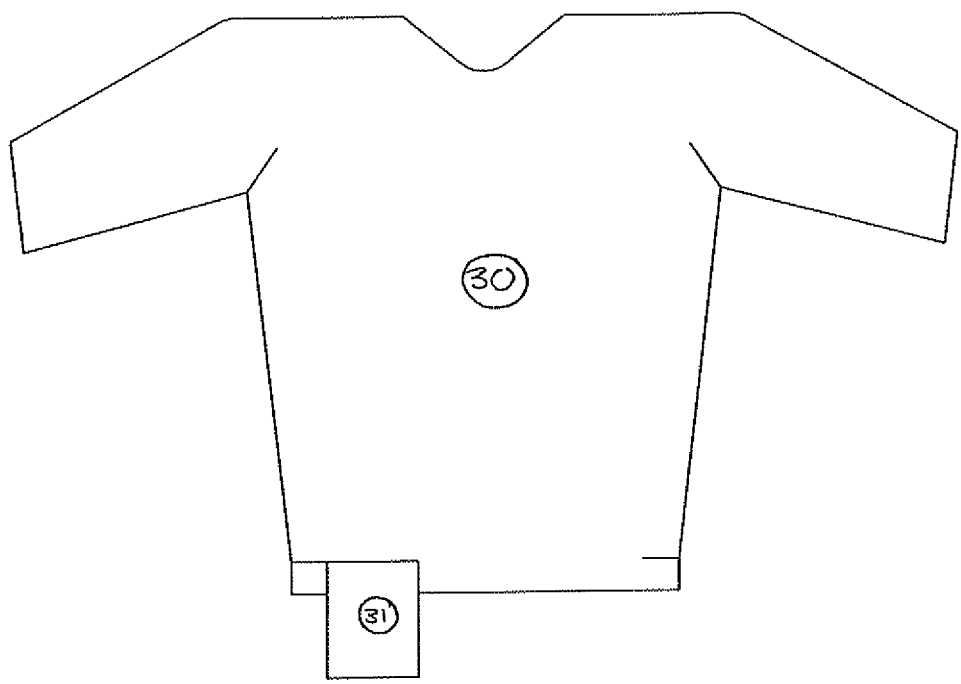
FIG. 5A illustrates a front view the garment shell 30. The garment houses the treatment hardware and is wearable beneath clothing. Also shown is the user interface and microcontroller 31.
Figure 5C:
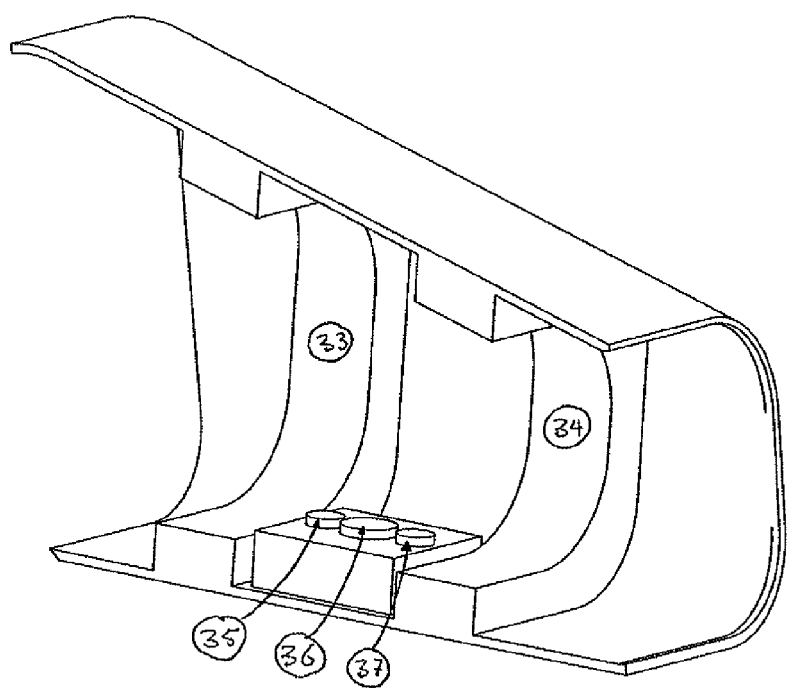
FIG. 5C is another view of the upper arm cuff.

FIGS. 5A, 5B and 5C illustrate a vest as a garment used in therapeutic treatment. Number 30 shows the garment shell. The garment houses the treatment hardware and is wearable beneath clothing. The user interface and microcontroller 31 is shown. The microcontroller is responsible for user input and controlling the various functions of the device and contains battery for portable use. The body heating element 32 is also shown. The heating element applies therapeutic levels of heat to the subject. The duration of heating and the temperature are determined by a microcontroller 30. Number 25 shows the ICT occlusion cuff. This is a pneumatic arm cuff capable of measuring blood pressure and inflating to suprasystolic pressure for ICT treatments. The pressure, duration, and number of cycles for ICT are determined by a microcontroller 30.

Also illustrated is the pulsatile cuff 26. This is a pneumatic arm cuff capable of measuring blood pressure and inflating in pulses before, during, or after ICT treatments. The pressure, duration, and frequency for the pulses are determined by a microcontroller 30. Also shown is the upper arm heating element 35. The heating element applies therapeutic levels of heat to the subject. The duration of heating and the temperature are determined by a microcontroller 30. Also shown is the upper arm muscle stimulation electrode 36. The electrode applies small amounts of current for therapeutic transcutaneous muscle stimulation. The amount of current, duration, and frequency of application are determined by the microcontroller 30. Lastly the upper arm vibration plate 37. The subject's arm is pressed against this plate to transmit therapeutic vibrations ranging from 3-50 Hz. The frequency and amplitude of the vibration are determined by a microcontroller 30.

Ischemic Conditioning and Vascular Shear Stress Therapy

Ischemic conditioning therapy induces ischemia in one or more peripheral locations of the subject's body followed by reperfusion. Inducement of ischemia is discussed in U.S. Pat. Nos. 8,246,548 and 8,551,008 which are hereby incorporated herein by reference in their entirety. Briefly, the therapy includes occluding an artery for a period of time followed by release of the occlusion causing reperfusion. There occlusion is typically induced in a limb of a subject. The reperfusion can continue for a selected period of time.

The occlusion may be created by various devices. In one embodiment, the occlusion is created by positioning an inflatable cuff around a subject's limb, inflating the cuff above systolic pressure, thereby occluding at least one artery such as the brachial or femoral artery. The occlusion is maintained for a preset duration. The cuff is deflated and the occlusion is removed. Blood flow returns to the limb, i.e., reperfusion. The reperfusion can be continued for a preset duration followed by one or more additional cycles of occlusion and reperfusion. The number and duration of each phase of the above described cycles can be controlled by a programmable microcontroller.

In another embodiment, a clamp-like device using a plunger, piston or screw device positioned above the artery may be used to create the occlusion.

The cycles of ischemia and reperfusion (ischemic conditioning therapy) may be controlled by a programmable microcontroller. The ischemic reperfusion cycle may be monitored. Devices used for monitoring can included but are not limited to thermometers or pulse oximeters. The device also includes actuators to inflate and deflate a cuff or to move a plunger on a clamping device. Actuators are also used in monitoring the therapy. As used herein, an actuator is any device, e.g., electrical, mechanical or chemical that causes movement or action.

Markers of ischemic conditioning include but are not limited to tissue oxygenation and temperature; markers of metabolism including lactate, pH, oxygen, carbon dioxide, ATP, ADP, adenosine, cytochrome oxidase, redox voltage, erythropoietin, bradykinin, opioids; and markers of blood flow or pulse.

The disclosure also combines ischemic conditioning therapy with vasculature shear stress conditioning. In one embodiment, vasculature shear stress conditioning induces arterial stress caused by movement of the blood during the diastole or relaxed phase of the heart beat. Normally, the blood is relative quiescent during this phase of the heartbeat. The therapy causes the blood to move through the artery creating stress on the endothelium cells comprising the wall of the artery. This aspect of the method subjects the subject's body, particularly the arterial system, to the stresses experienced during exercise.

In an embodiment of the invention, a scheduled series of transient ischemic episodes is applied in combination with brief partial occlusion of the same or different portion of the subject to induce increased shear stress along the endothelium walls of the arteries and veins. The actuation of these partial occlusions pulse the blood within the arteries and veins, creating the shear stress. These occlusion episodes may be controlled by the microcontroller. In a preferred embodiment the duration of the occlusion episode may be timed to be contemporaneous with the diastolic phase of the heart rhythm, i.e., 2 to 5 seconds duration, followed by release of the occlusion at the initiation and for the duration of the systolic phase of the heart rhythm.

In another embodiment, shear stress is induced by placing a separate inflatable occluding cuff distal of the first occluding cuff (used for ischemic conditioning) on one or more extremities such as the arms. It will be appreciated that this is the same limb used for ischemic conditioning therapy as well as vascular shear stress conditioning. The first cuff can be controllably inflated to occlude the portion of the arm distal from the cuff. This occlusion can be for example 5 minutes in duration, followed by 5 minutes of reperfusion (i.e., ischemic conditioning). This cycle can continue for a duration of 20 minutes, for example. The second distally positioned cuff can be controllably inflated for a duration of 2-5 seconds followed by release for two to five seconds. This cycle can be continued for a duration of 20 minutes or longer. It will be appreciated that the cycle of the second distally positioned cuff (second cuff) is not required to be synchronized with the subject's heart beat. This embodiment is unlike enhanced external counterpulsation and is termed vasculature shear stress conditioning.

Figure 6A:
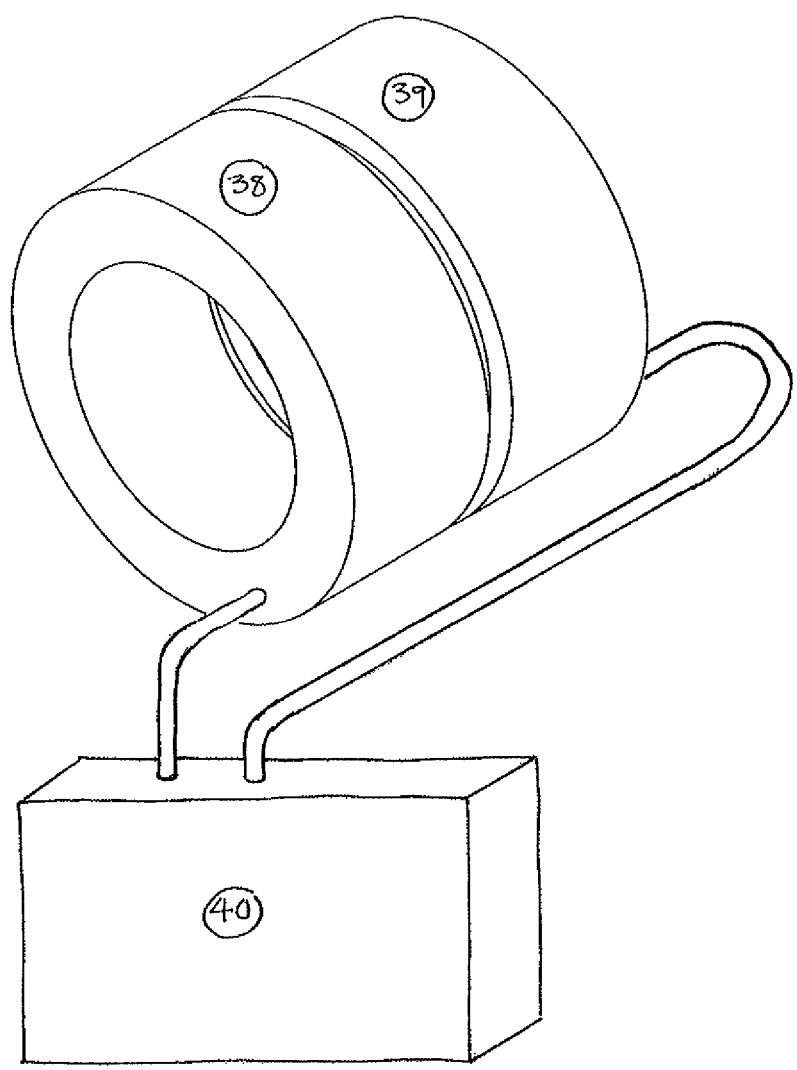
Figure 6B:
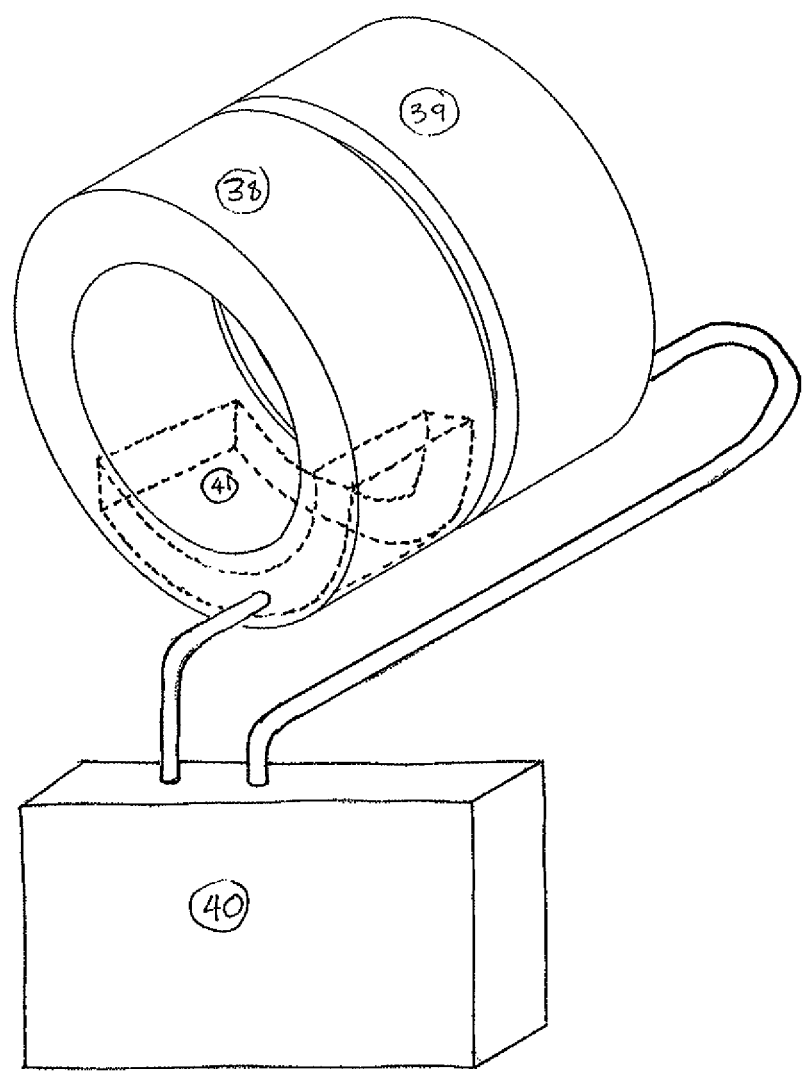

It will further be appreciated that the above described combined ischemic conditioning therapy and vasculature shear stress therapy can utilize a combined cuff device. See FIGS. 6A, 6B and 6C. See also FIGS. 3 and 4 as described herein. The dual mode cuff is a pneumatic cuff that contains two separate bladders. Each bladder is a self contained unit that is controlled, housed and operated independently of the other inflatable bladder via a microcontroller 40. The construction of the cuff involves two separate chambers; the distal chamber 38 and the separate proximal chamber 39. Each bladder can be separately inflated and deflated. Each chamber contains an inflatable bladder (distal bladder 41 and proximal bladder 42). The microcontroller can be housed together with the actuators responsible for the operation of the cuffs.

In this embodiment, the device contains two inflatable bladders. One bladder (first cuff 39) is positioned proximally and is inflated above stytolic pressure to occlude an artery. The second portion or segment bladder 38 of the device is positioned distally and is used to pulsate the blood within the arteries and veins of the occluded limb. An embodiment of this device is depicted in FIG. 3C.

In another embodiment of vasculature shear stress conditioning, a cuff (third cuff) can be placed around the calf (lower leg) of the subject's leg.

Figure 7:
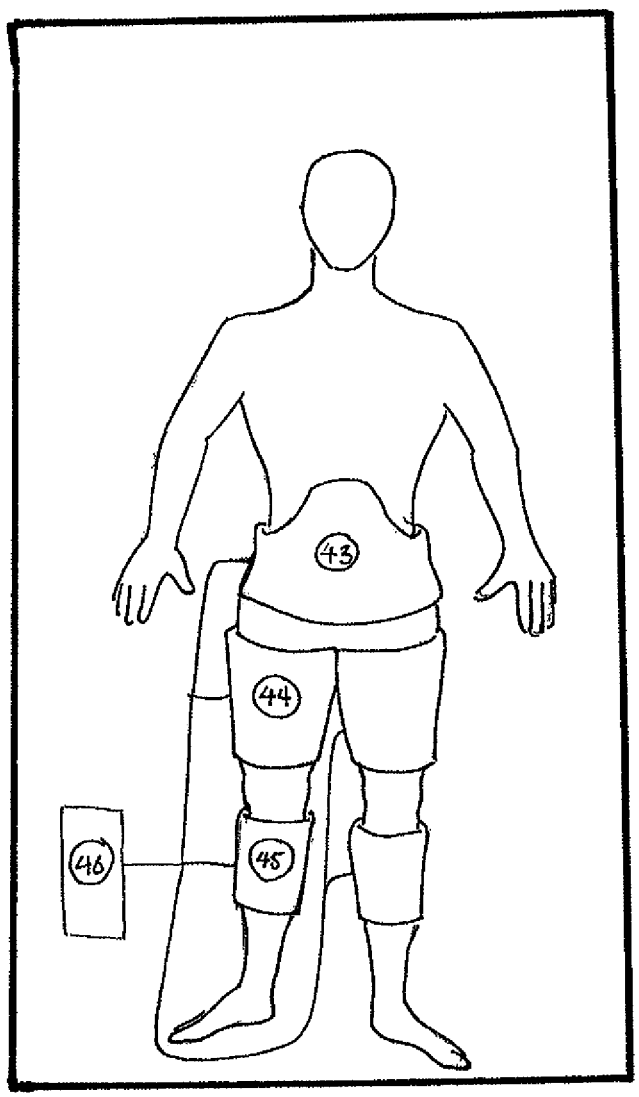
FIG. 7 illustrates an abdominal and lower back cuff 43. Also illustrated is a lower leg cuff 45 and upper thigh cuff 44.

FIGS. 1A and 1B show this embodiment used on a treatment bed. It will be appreciated that this cuff 3 placed over the lower leg will preferably be a separate limb than used for the simultaneous ischemic conditioning therapy. An additional cuff (fourth cuff) 2 can be placed over or around the subject's thigh. See also FIG. 7 showing a cuff around a subject's upper leg 44. The fourth cuff 45 (over the lower leg in FIGS. 1A and 1B) is proximally positioned relative to the third cuff 44. In another embodiment, a fifth inflatable device 43 surrounds the subject's hips or pelvis. It can extend to the abdomen and lower back. Inflation of each cuff can be separately controlled by the microcontroller. Continuing with FIG. 7, the abdominal and lower back cuff (fifth cuff) extends up along the surface of the abdomen and lower back 43. The cuff is capable of housing and delivering different treatment modalities, including but not limited to, electrical muscle stimulation, heat, and vibration on both sides of the device, i.e., abdomen and back. The various parameters of these treatments are determined by the microcontroller 46. The upper leg cuffs 44 and lower leg cuffs 45 are both pneumatic cuffs that can inflate and maintain a pressure determined by the microcontroller. The fifth cuff 43 is capable of inflating in a pulsatile fashion synchronized with the inflation of the lower leg and upper leg cuffs.

See FIG. 1A (2, 3) The timing of the inflation of the cuffs of FIGS. 1A and 7 can be synchronized with the systolic/diastolic pattern of the heart beat rhythm. This can utilize an electrocardiogram machine (not shown) attached to the subject's chest and attached to the microcontroller. In one embodiment shown in FIG. 1A, inflation of the third (most distal) cuff 3 is initiated first, followed immediately by the fourth cuff 2 and then the fifth cuff surrounding the pelvis, abdomen and lower back. See FIG. 7 also 45, 44, and 43.

It will be appreciated that this synchronized initiation of inflation induces a retro flow of blood toward the subject's torso. It will further appreciated that vasculature stress conditioning creates shear stress along the endothelial walls of the arteries and veins during a period the heart is at rest and blood flow volume is minimized. The inducement of shear stress mimics the effect of strenuous exercise upon the subject's vasculature. It triggers the production of beneficial compounds such as nitric oxide enhancing the ability of the vasculature to dilate. For example, increases in nitric oxide and adenosine bioavailability are known to occur after an ischemic episode. These compounds are well known to relax smooth muscle cells and decrease arterial stiffness over time. In the instant embodiment described above, the treatment does not create an ischemic episode, i.e. hypoxia is not created.

Perfusion of downstream tissues is further augmented by flow-mediated dilation (FMD) of larger conduit arteries, which acts to prolong the period of increased blood flow. As a consequence of the elevated blood flow induced by reactive hyperemia, downstream conduit vessels undergo luminal shear stress. Endothelial cells lining the arteries are sensitive to shear stress and the stress induces in opening of calcium-activated potassium channels and hyperpolarization of the endothelial cells with resulting calcium entry into the endothelial cells, which then activates endothelial nitric oxide synthase (eNOS). Consequent nitric oxide (NO) elaboration results in vasodilation. Endothelium-derived hyperpolarizing factor (EDHF), which is synthesized by cytochrome epoxygenases and acts through calcium-activated potassium channels, has also been implicated in flow-mediated dilation. Endothelium derived prostaglandins are also thought to be involved in flow-mediated dilation. This has a synergistic effect with the vasculature shear stress and vibration therapies.

The therapeutic effects of conditioning are mediated by changes to the vasculature and/or the neurovasculature, as well as anti-inflammatory effects. Nitric oxide (NO) bioavailability may be improved locally. Nitric oxide (NO) has been shown to be involved in cutaneous active vasodilation induced by systemic application of heat on the basis that local inhibition of NO synthase results in inhibition of cutaneous local perfusion while local perfusion of the NO donor, sodium nitroprusside, results in maximum local cutaneous perfusion. Similarly, it has been found that NO mediates vasodilatation in response to local application of heat. Conversely, local cooling induces cold-sensitive afferent nerves to activate sympathetic nerves to release norepinephrine, which leads to local cutaneous vasoconstriction.

The apparatus of the disclosure consists of multiple air inflatable cuffs that may be attached around the subject's extremities. For example, cuffs may be attached to one or both upper arms of the subject. Cuffs may be attached to lower leg or to the calves of each of the subject's legs. Cuffs may be also attached to both upper thighs of the subject. An additional cuff may surround the pelvic region.

The cuffs attached to the upper arm can be inflated to occlude the brachial artery for a specified duration, then deflated to allow reperfusion of the arm with blood. The occlusion/reperfusion cycle can be monitored by temperature recording devices. See FIGS. 8A, 8B, and 8C and the accompanying discussion herein. These devices can be placed, for example, on a finger of the subject's hand. Before occlusion, the skin temperature (as measured by the thermal sensors) are at equilibrium or at a baseline temperature. During periods of occlusion, the temperature of the skin in the effected area drops. After the occlusion is removed, the temperature of the affected area briefly surges above the baseline temperature and then returns to the baseline.

Stated in greater detail, a sensitive fingertip temperature sensor monitors, records, and analyzes fingertip temperature during the ischemic conditioning cycle (cuff occlusion and release procedure). Temperature changes serve as a surrogate marker of blood flow changes that result from vascular reactivity. In one embodiment of the DTM procedure, an automated procedure is initiated beginning with an automated blood pressure measurement, followed by cuff occlusion of the right arm. During the cuff occlusion (2 to 5 minutes), fingertip temperature in the right hand falls because of the absence of warm circulating blood. Once the cuff is released, blood flow rushes into the forearm and hand, causing a temperature rebound (TR) in the fingertip which is directly proportional to the vascular reactivity. The higher the temperature rebound (TR), the better the vascular reactivity. The release of the occlusion generated by the inflated cuff results in reperfusion which mimics the relaxation of the limb after extended exercise.

It will be appreciated that in one embodiment the finger tip is isolated, i.e., enclosed in insulative material. In one embodiment the combined therapies can be implemented during sleep. The protective insulation avoids the subject's hand resting against another body part or other heat source. The subject may wear brain activity monitors (not shown) to allow the therapy to be administered during selected phases of sleep. The disclosure teaches administration of the therapy during the phase of sleep achieving minimal reception of pain and perception.

The cuffs attached to the subject's leg and pelvic region can be operated in coordination with the systolic/diastolic rhythm of the heart. The method for assessing endothelial function is provided that comprises providing a vasodilating stimulant to a subject to stimulate hemodynamic activity in a selected region of the subject's body monitoring a change in a hemodynamic parameter at the selected region, and assessing the subject's endothelial function based upon said monitoring, illustrated at block. In one embodiment, the monitored hemodynamic parameter may be a parameter such as blood temperature, blood oxygen content, blood flow rate, or the like, or a combination thereof.

The combination of ischemic conditioning therapy and vasculature shear stress therapy induces elevated levels of $CO_2$ and decreased levels of oxygen in the blood. Also there is an increase in NO inducing dilation of the vessel walls. The product of these combined therapies is to mimic the effects of exercise on the subject's body. Benefits of exercise include reduced blood pressure, improved cardiovascular function, improved endothelial function and reduced inflammation. The combined therapies taught by this disclosure are the same, i.e., improved cardiovascular function, improved endothelial function and reduced inflammation.

It will be appreciated that in performing these combined therapies, the patient's heart rate need not change. Exercise training improves endothelium-dependent vasodilatation both in epicardial coronary vessels and in resistance vessels in patients with atherosclerosis, coronary artery disease or chronic heart failure. Increased release of nitric oxide through continued physical exercise alleviates impairment of reactive hyperemia in patients with essential hypertension. See Sackner et al., U.S. Pat. No. 7,090,648.

The invention relies, at least in part, on physiologic reactions to ischemia and pulsatile shear stress. Brief periods of ischemia (a local shortage of oxygen-carrying blood supply) in biological tissue, render that tissue more resistant to subsequent ischemic insults or events (such as oxygen deprivation) through several mechanisms including through increased vasodilative capacity. Ischemic conditioning exerts protection and appears to be a ubiquitous endogenous protective mechanism at the cellular level that has been observed in the heart of humans and every animal species tested. This protection has also been seen in organs such as the liver, kidney, gut, skeletal tissue, urinary bladder and brain. In fact, ischemic conditioning can have an effect on any proliferative tissue, e.g. skin, hair, and bone marrow.

In one embodiment of the invention, transient ischemia is implemented by cuffs or straps that are secured over or around one or more of the limbs of the subject, as depicted in FIGS. 1A and 1B. As shown in FIG. 1A, the occlusive cuffs or straps 1, 2 and 3 can be placed over one or more locations for compression sufficient to occlude blood flow to the hands and or feet. For example, for occlusion of blood supply to the hands, compression can be applied to the upper arm 1 over the brachial artery, the lower arm over the radial and ulnar arteries, or the wrist over the radial artery. For occlusion of blood supply to the feet, compression may be applied to the upper leg over the femoral and deep femoral arteries, or to the lower leg over the tibial arteries. In one embodiment, the cuffs are inflatable and inflation results in sufficient pressure around the circumference of the limb to result in occlusion of the arterial blood supply to the limb. In one embodiment, ischemic conditioning can be administered with cuffs on both arms and both legs. In one embodiment, the subject wears an inflatable belt or band around the pelvis.

As previously discussed, in one embodiment the microcontroller initiates inflation first in the cuff of the lower leg 3, followed in sequence by inflation of the cuff or occlusion device over the subject's thigh 2. In an embodiment not shown there is a further inflatable cuff over the subject's pelvic region. Inflation of this pelvic cuff follows in sequence the inflation of the lower leg cuff 3, and the cuff over the thigh 2. This pushes the blood toward the torso of the subject.

The duration of ischemia varies by therapeutic targets, but is typically provided for a period from about 1 to about 20 minutes, preferably from about 2 to about 5 minutes, followed by release of the occlusion. Occlusion and release (reactive hyperemia) procedures with different occlusion times are implemented depending on individual tolerance and response to therapy as well as the planned treatment schedule such that a desired distal and or contralateral vascular/neuro/neurovascular function is obtained. Repeated cuff occlusion and release is tailored to improve vasoreactivity (increasing the vasodilative capacity) including by improving nitric oxide bioavailability (reducing destruction or increasing production). This effect can be seen in the same distal extremity as the cuff inflation but is also expected to have neurovascular mediated systemic vasodilation as well.

In one embodiment of the invention, a programmable cuff inflation and deflation device is employed to provide intermittent scheduled transient ischemia. The device can inflate one or more cuffs on one or more body parts at a time. The method induces reactive hyperemia and can mimic the effects of local exercise. For example the availability of oxygen in the blood is decreased with resulting increased production of nitric oxide dilating the walls of the vascular lumen. The larger the area of ischemia, the higher the hyperemia.

A portable form of the device is implemented for ambulatory use such as the embodiment depicted in part in FIG. 4. In the embodiment depicted in FIG. 4, one or more occlusive cuffs 25, 26 are in electrical connection with microcontroller which may be worn anywhere on the body. The inclusive cuff can be inflated by an electric pump associated with the programmable monitor, which also can be adapted to record the pattern of occlusion. Alternatively, the cuff(s) can be manually inflated at intervals. In one embodiment, the cuff(s) are manually inflated in response to a signal given by a microcontroller that instructs inflation and deflation of the inflatable cuff(s). In another embodiment, the monitor instructs manual tightening and loosening of one or more straps in accordance with a programmed schedule.

Inherent skin temperature means the unaltered temperature of the skin. This is in contrast to an induced skin temperature measurement which measures perfusion by clearance or wash-out of heat induced on the skin. Various methods of recording of inherent skin temperature on a finger tip or palm distal to an occlusive cuff are disclosed in Naghavi et al., U.S. application Ser. No. 11/563,676 and PCT/US2005/018437 (published as WO2005/118516) which are incorporated by reference herein. The combination of occlusive means and skin temperature monitoring for determination of vascular reactivity has been termed Digital Temperature Monitoring (DTM) by certain of the present inventors. In one standard utilization, DTM employs a standard arm-cuff vascular reactivity procedure, which includes a temporary occlusion of blood flow in the arm. During the cuff occlusion, the lack of blood flow (ischemia) elicits a microvascular dilative response (opening small vessels). Upon releasing the cuff, blood flow rushes into the forearm and hand, not only restoring baseline flow but also resulting in an overshoot (reactive hyperemia). This overshoot causes shear stress in the larger (conduit) arteries, which stimulates these arteries (macrovessels) to dilate and accommodate the increased blood flow.

Figure 8A:
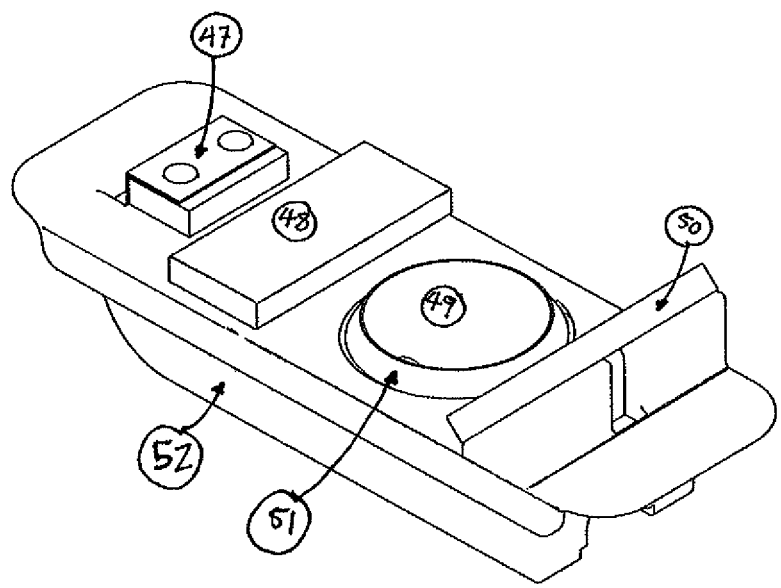
FIGS. 8A, 8B and 8C illustrate various views of a temperature recording device. Illustrated are the photoplethysmography component 47, the proximal adhesive pad 48, temperature sensor 49, distal adhesive pad 50 insulation 51 and plastic shell 52.
Figure 8B:
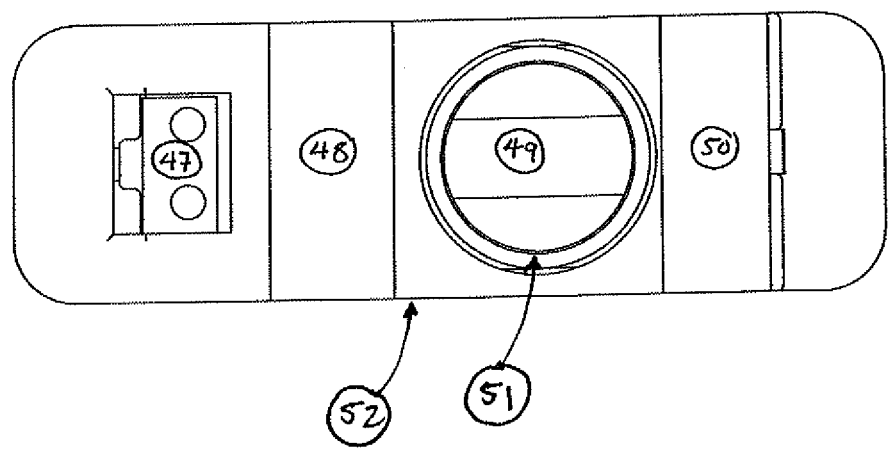
Figure 8C:
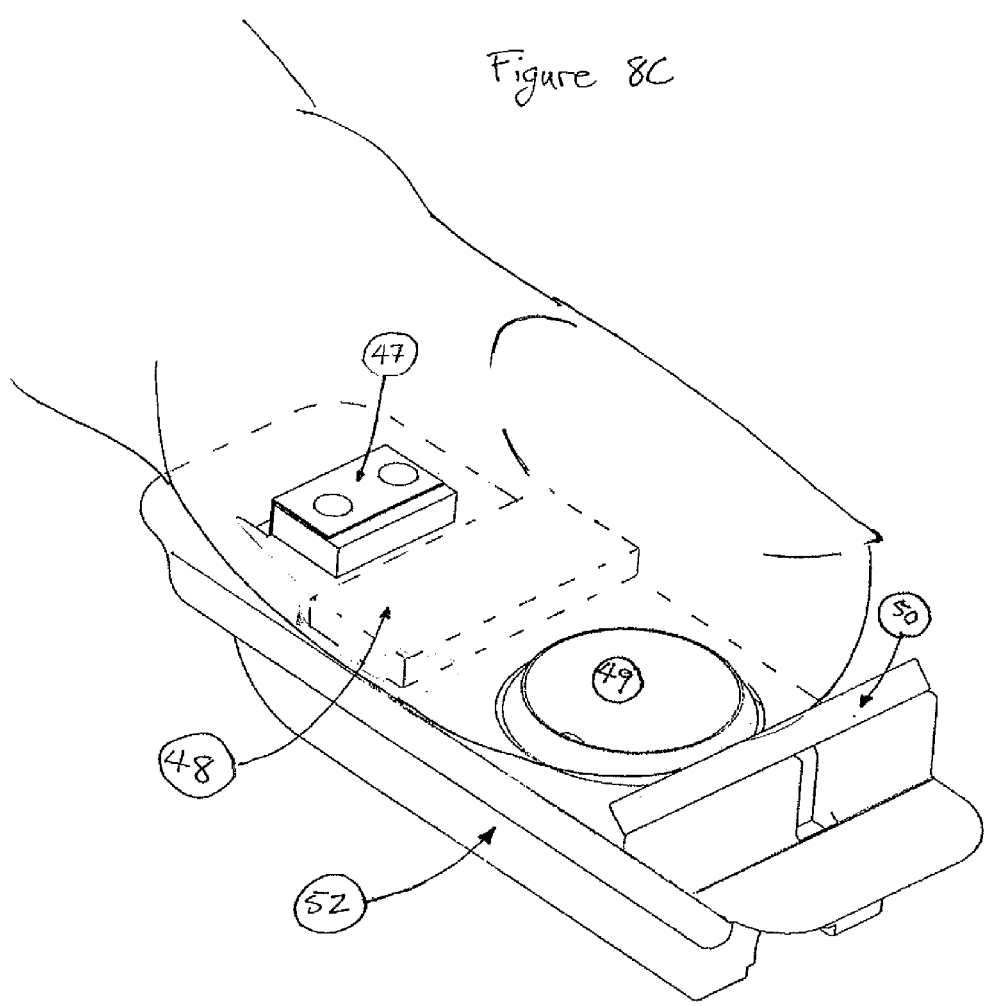

FIGS. 8A, 8B and 8C depict use of digit monitor, e.g., fingertip monitor, in conjunction with a blood flow occlusive device located on an upper or lower extremity. Illustrated are the photoplethysmography (PPG) 47, proximal adhesive pad 48, temperature sensor 49, distal adhesive pad 50, insulation (optional) 51 and plastic shell 52. The photoplethysmography (PPG) and Digital Thermal Monitoring (DTM) sensor is a combined sensor that utilizes two different modalities to obtain biometric data from the subject's digit. The probe is composed of a plastic shell 51 that houses both the DTM 49 and the PPG 47 sensors. The probe is fixed to the digit by way of two disposable adhesive pads; the distal adhesive pad 50 and the proximal adhesive pad 48. The DTM sensor may be insulated from outside heat sources with insulation foam. When placed on the digit, the insulation foam insert ensures that the DTM sensor will only be affected by the temperature of the fingertip.

Figure 3A:
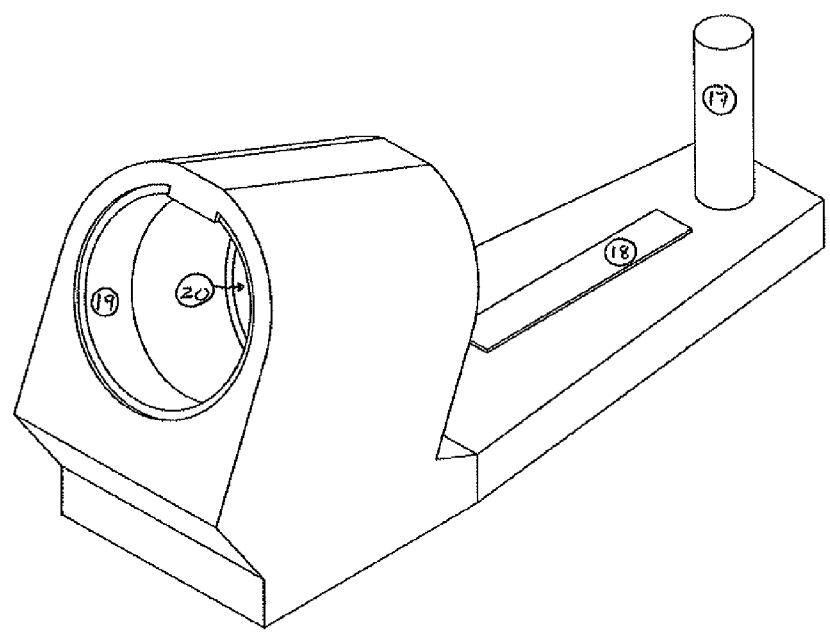
FIG. 3A illustrates hand vibration bar 17. Also shown is a forearm heating element 18. Also illustrated is an ICT occlusion cuff 19 and a pulsatile cuff 20.
Figure 3B:
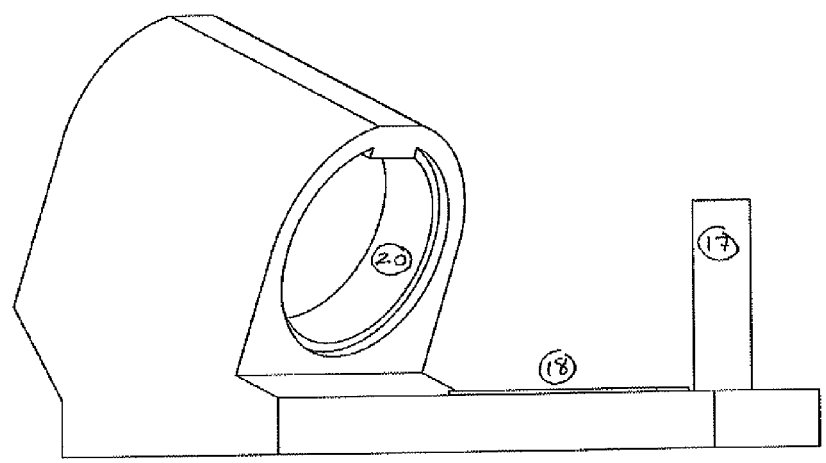
FIG. 3B illustrates another perspective view of the arm device.
Figure 3D:
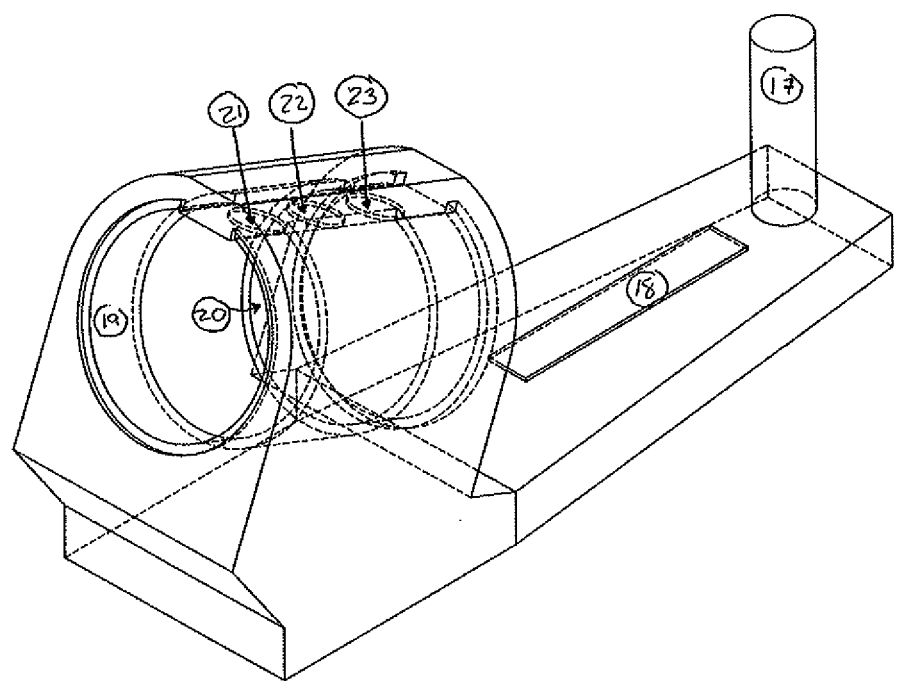
FIG. 3D is a perspective view of the arm treatment device.

In the depicted embodiment of FIG. 3a, the fingertip monitor is a DTM that monitors fingertip temperature in conjunction with induced reactive hyperemia in order to provide a surrogate marker of vascular reactivity as a result of repeated ischemic conditioning. In the depicted embodiment of, an artificial pulse generator is included to provide an artificial pulse and fingertip monitor is, or includes, a pulse oximeter.

In one embodiment the pulse generator effects mechanical actuation by pulsating fluid pressure in a cuff to cause mechanical disturbance of arterial blood. In other versions, repetitive, external electromechanical actuation provides the artificial pulse. In still other versions, the artificial pulse is generated by external non-mechanical optical illumination utilized to imitate the absorption patterns of a pulsatile blood flow signal by oscillating the intensity of a light source of either a single or multiple wave length. The optional extremity mounted monitor is adapted to display one or more of program parameters, ambient temperature, blood pressure, DTM parameters of fingertip temperature over time, and pulse oximetry data.

In one embodiment, the method for monitoring the vascular or neurovascular response further includes simultaneously measuring and recording additional physiologic parameters including pulse rate, blood pressure, galvanic response, sweating, core temperature, and/or skin temperature on a thoracic or truncal (abdominal) part.

In one embodiment of the invention, metabolic endurance and athletic performance can be improved by repeated, scheduled ischemic conditioning treatments. Such treatments provide a natural stimulus for the metabolic machinery (mitochondrial activity, intracellular genes, mRNA, proteins) of the ischemic tissue to better adapt itself to anaerobic conditions, such as those encountered during prolonged exercise and continuous, strenuous activity. Repeated ischemic conditioning treatments are expected to induce metabolic changes and adaptation similar to that induced by exercise conditioning. Ischemic conditioning modulates the supply component, whereas exercise conditioning modulates the demand component. The intracellular metabolic machinery responds to the balance between supply and demand for oxygen and other required nutrients. A decrease in supply (ischemia) or an increase in demand (exercise) will trigger a similar response.

The invention relies, at least in part, on physiologic reactions to ischemia. Brief periods of ischemia (a local shortage of oxygen-carrying blood supply) in biological tissue, render that tissue more resistant to subsequent ischemic insults through several mechanisms including through increased vasodilative capacity.

Ischemic conditioning has been shown to produce tolerance to reperfusion damage from subsequent ischemic damage. One physiologic reaction to local ischemia in normal individuals is reactive hyperemia to the previously ischemic tissue. Arterial occlusion results in lack of oxygen (hypoxia) as well as an increase in vasoactive metabolites (including adenosine and prostaglandins) in the tissues downstream from the occlusion. Reduction in oxygen tension in the vascular smooth muscle cells surrounding the arterioles causes relaxation and dilation of the arterioles and thereby decreases vascular resistance. When the occlusion is released, blood flow is normally elevated as a consequence of the reduced vascular resistance.

The therapeutic effects of conditioning are mediated by changes to the vasculature and/or the neurovasculature, as well as anti-inflammatory effects. Nitric oxide (NO) bioavailability may be improved locally. Nitric oxide (NO) has been shown to be involved in cutaneous active vasodilation induced by systemic application of heat on the basis that local inhibition of NO synthase results in inhibition of cutaneous local perfusion while local perfusion of the NO donor, sodium nitroprusside, results in maximum local cutaneous perfusion. Similarly, it has been found that NO mediates vasodilatation in response to local application of heat. Conversely, local cooling induces cold-sensitive afferent nerves to activate sympathetic nerves to release norepinephrine, which leads to local cutaneous vasoconstriction.

Although originally described as conferring protection against myocardial damage, preconditioned tissues have been shown to result in ischemia tolerance through reduced energy requirements, altered energy metabolism, better electrolyte homeostasis and genetic re-organization, as well as reperfusion tolerance due to less reactive oxygen species and activated neutrophils released, reduced apoptosis and better microcirculatory perfusion compared to non-preconditioned tissue.

In one embodiment of the present invention, intermittent transient ischemia is induced in one or more limbs, or portions thereof, of a subject. The intermittent transient ischemia stimulates and conditions the downstream vasculature and thereby prevents or reduces symptoms of the chronic medical condition.

In one alternative embodiment, local ischemia of the superficial skin layers is provided by an inflatable mitten, sock or glove that operates to provide compression against the skin and thus restrict normal blood flow to the superficial tissues. As with ischemia induced by blockage of blood flow by compression over an artery such as by inflation of a blood pressure cuff, the induction of superficial pressure can be implemented according to a schedule of transient induced pressure as the treatment or conditioning requires. Several other embodiments for inflatable compression are possible such as for example a full body suit that can be used to provide ischemia to the superficial skin layers.

The present method of administering one or more transient ischemic episodes to one or more limbs according to a schedule is neither dangerous nor expensive and may be readily implemented in every subject. In one embodiment, cuffs are placed on both arms and legs for ischemic conditioning. The device can be implemented for either in-subject or, preferably, outpatient treatment. The transient ischemic episodes provide positive physiological effects by several mechanisms including without limitation: increased nitric oxide bioavailability, increased scavenging of free radicals and reduction of inflammation. If administered in a series of episodes over a sufficiently amount of time, the method is expected to increase vasodilative capacity including by increased arterial and smooth muscle flexibility, as well as increases in functional capillary density, and may be further expected to hasten wound healing.

Ischemic Conditioning, Vasculature Shear Stress Conditioning and Electrical Muscle Stimulation In another embodiment, transient ischemic conditioning and vasculature shear stress conditioning can be combined with electrical muscle stimulation, wherein one or more groups of the subject's muscles are contracted in response to electrical stimulus. This stimulation occurs simultaneous to the ischemic reperfusion conditioning and the shear stress conditioning. In a preferred embodiment, the electrodes of the electrical muscle stimulation device are placed on the subject's skin in close proximity to a peripheral nerve controlling a muscle group. Electrical stimulation of the nerve triggers contraction of the muscle group. Repeated contractions of the muscle group increase metabolism of calories. Repeated contractions also induce the release of endorphins into the blood stream. This elevation of endorphin levels further mimics the effect of prolonged or strenuous exercise. In one embodiment, the electrical muscle contractions can continue for up to 60 minutes with a preferred duration of 20 to 30 minutes.

In yet a further embodiment, electro-muscular stimulating devices can be placed on selected locations of the subject's skin surface. The electro-muscular simulating devices may be placed proximate to one or more muscle groups of the subject. Even more preferred is placing the electro-muscular stimulating devices proximate to a peripheral nerve of the subject's body. This induces neural stimulation of a muscle group. It will be appreciated that increasing the distance between individual electrodes will increase the depth of tissue affected by the current. In one embodiment, the electro-muscular stimulating device may be part of the structure of an inflatable or clamp device.

As discussed, in the preferred embodiment, the frequency of partial or whole body vibration therapy will be low, i.e., less than 80 Hz and preferably less than 30 Hz.

As used herein, actuator means a device (electrical, mechanical or chemical) that puts something into motion or causes movement or triggers another device to begin operating. The electrodes stimulating nerve or muscle tissue would be an actuator. A system implementing the disclosure employs actuators, e.g., inflating the cuff or during the clamp on an occlusion device. Another example is generating an electrical pulse, including amplitude, duration, and frequency.

As stated in this disclosure, transcutaneous electrical muscle stimulation may be used simultaneously with ischemic conditioning therapy. In one embodiment, the stimulation source (electrodes placed on the subject's skin are located proximate to one or more peripheral nerves. Muscle contractions utilize intracellular oxygen and increases the $CO_2$ levels in the blood, thus complementing the effect of ischemia. Repetitive contractions of the affected muscles will strengthen those muscles. The application of electrical muscular stimulation can be performed prior to exercise. This practice is also applicable to ischemic conditioning therapy. The hemodynamic markers of the subject may be monitored. Hemodynamic markers include but are not limited to tissue oxygenation and temperature; markers of metabolism including lactate, pH, oxygen, carbon dioxide, ATP, ADP, adenosine, cytochrome oxidase, redox voltage, erythropoietin, bradykinin, opioids; and markers of blood flow or pulse. Monitoring of these markers can also facilitate adjustment of the program setting controlled by the microcontroller.

In another embodiment of the disclosure, the electrodes may be implanted into the subject's tissue. In another embodiment the device may be an electromagnetic stimulator. In yet another embodiment, the disclosure can be implemented utilizing other devices including but not limited to a hospital patient bed, a nursing home bed, an operating room bed, a wheelchair, an athletic performance bed, a rehabilitation bed, a rehabilitation suit, a space suit, a flight suit, a flight jacket, a vest, an armband, a pair of boots, or an orthopedic brace. The embodiment of the disclosure pertaining to the combination of ischemic conditioning and electrical muscular stimulation can also be used to enhance performance of a left ventricular assist device.

Ischemic Conditioning, Vasculature Shear Stress Conditioning and Vibration Therapy Vibration has been shown to improve blood flow, particularly in the skin. Increases in muscle flexibility and strength, secretion of hormones important in the regeneration and repair process, blood flow, and strength of bone tissues has been attributed to whole body vibration (WBV) combined with exercise. *The Effect Of Whole Body Vibration On Lower Extremity Skin Blood Flow In Normal Subjects*, Everett B. Lohman III, Jerrold Scott Petrofsky, Colleen Maloney-Hinds, Holly Betts-Schwab, Donna Thorpe, © Med Sci Monit, 2007; 13(2): CR71-76

Vibration also induces vasculature shear stress by the movement of blood within the subject's lumans. Vibration pads can be utilized on the floor, bed or chair. They can also be utilized in specialized garment such as athletic training apparel and space suit (where the subject may be exposed to prolonged periods of weightlessness with resulting loss of bone density and muscle mass).

It will be appreciated that each embodiment of the disclosure physiologically replicates the effect on the subject's body of physical exercise without significantly affecting the heart rate of the subject. This creates an advantage over the increased heart rate problem faced by many exercise-induced ischemic vascular reactivity measures such as treadmill stress testing. Thus, ischemic conditioning is able to simulate ischemic effects of exercise but avoid associated problems.

Such treatments provide a natural stimulus for the metabolic machinery (mitochondrial activity, intracellular genes, mRNA, proteins) of the ischemic tissue to better adapt itself to anaerobic conditions, such as those encountered during prolonged exercise and continuous, strenuous activity. Repeated ischemic conditioning treatments are expected to induce metabolic changes and adaptation similar to that induced by exercise conditioning. Ischemic conditioning, combined with vasculature shear stress conditioning and electrical muscle stimulation, modulates the supply component, whereas exercise conditioning modulates the demand component. The intracellular metabolic machinery responds to the balance between supply and demand for oxygen and other required nutrients. A decrease in supply (ischemia) or an increase in demand (exercise) will trigger a similar response.

In an embodiment, other chronic medical conditions can also benefit from scheduled ischemic conditioning and the resulting increase in perfusion, relaxation of smooth muscle cells, vasodilation, and elaboration of anti-inflammatory and anti-oxidant mediators. For example, microvascular dilative capacity is hindered and inflammation is increased in Raynaud's syndrome and several associated disorders such as scleroderma (a collagen-related immune disorder) and small vessel vasculitis (including vasculitis associated with anti-neutrophil cytoplasmic antibodies, or ANCAs). Treatment of hypertension will also benefit from this combined treatment program. Further, diabetes, insulin resistance, high blood glucose, and several other metabolic disregulations are well known to exacerbate inflammation and oxidation. Even further, subjects with chronic coronary conditions that reduce ejection fractions and perfusion can benefit from the effects of ischemic conditioning. For example, chronic coronary heart disease subjects, heart failure (especially the more severely symptomatic such as in Class III and IV subjects), ischemic heart, and stable angina can exhibit chest pain upon exercise which limits the capacity for physical conditions. However, these subjects can receive similar benefits of exercise by episodes of ischemic conditioning. Physical conditioning the extent tolerable is expected to increase the benefits of the ischemic conditioning provided herein.

The disclosure also includes the combination of ischemic conditioning therapy, vascular shear stress conditioning, electrical muscle stimulation and vibration conditioning. The combination of ischemic conditioning and vascular shear stress greatly affects the subject's endothelium by causing factors including but not limited to dilation of the vessel wall, smoothing the endothelium cell and increasing NO production. Also induces electrical stimulation (involuntary muscle contraction) to one or more groups of the subject's muscles. Electrical stimulation also combines with ischemic conditioning to increase the $CO_2$ levels in the blood while decreasing the oxygen content. The electrical stimulation of muscles increases endorphin levels in the blood. As stated previously, the disclosure creates the physiological effects of exercise without creating cardiac stress. It is a program suitable for subjects suffering from coronary artery disease or other impairment.

The disclosure also claims a combination therapy of ischemic conditioning, vasculature shear stress and electrical muscle stimulation. Specifically a system and method for inducing physiological effects of ischemic conditioning, physiologic effects of shear stress, and physiological effects of electrical stimulation in a subject's body. The system includes a device for creating ischemia on a portion of the subject's body, e.g. an inflatable cuff, tourniquet, or clamp, a second device to create vascular shear stress, e.g., a cuff or series of cuffs and a third device to cause an electrical stimulation of one or more nerves or one or more muscles, a device to monitor hemodynamic markers including tissue oxygenation and temperature; markers of metabolism including lactate, pH, oxygen, carbon dioxide, ATP, ADP, adenosine, cytochrome oxidase, redox voltage, erythropoietin, bradykinin, opioids; and markers of blood flow or pulse, a microcontroller and a first actuator to cause the first device to cause ischemia in a subject's body part for a preset duration and then stop the ischemia for a preset duration, and to repeat the ischemia and reflow periods according to a preset program; a second actuator to simultaneously cause the second device to mechanically generate arterial shear stress according to a preset program of mechanical pulse amplitude, duration, and frequency; a third actuator to simultaneously cause the third device to electrically stimulate a nerve or muscle, or a combination thereof, according to a preset program of electrical pulse amplitude, duration, and frequency; and a fourth device to concurrently monitor one or more hemodynamic markers or markers of ischemia.

In another embodiment, at least one ischemic conditioning treatment of induced ischemia or hypoxia, and/or application of heat, is combined with non-pharmacologic techniques for modulating the autonomic nervous system (ANS), mostly for regional and transient modulation based on anatomical reflex zones. These non-pharmacologic techniques may include non-invasive electric, magnetic, or electromagnetic neuro-modulating devices used to increase local ANS activity. In another embodiment, transient intermittent ischemia and or heating is combined with hand exercises to increase demand and thereby improve nitric oxide bioavailability in the target areas.

Enhanced Athletic Training

With the teachings of this disclosure it is possible to achieve enhanced exercise training and physical performance by monitoring exercise and supplementing exercise with the conditioning programs taught by this disclosure, i.e., combined ICT with vasculature shear stress conditioning or ICT, vasculature shear stress conditioning and electro muscular stimulation. In addition, these protocols can be combined with heat and vibration.

It is worth remembering that athletic competitions among highly trained athletes may be decided by mere hundredths of a second. Therefore, any training protocol which gives the slightest advantage can be highly advantageous. For example, it has been shown that the application of heat induces dilation of subcutaneous lumens. Similarly, it has been found that NO mediates vasodilatation in response to local application of heat. This increases the flow of blood through the lumen, thereby amplifying the effect upon the endothelium during ischemic and reperfusion conditioning or during vasculature shear stress conditioning. Application of cutaneous heat in a range of 100° F. to 105° is preferred although higher temperatures can be utilized under supervision.

Similarly, vibration therapy in conjunction with vasculature shear stress conditioning may be especially valuable. Vibration of the body will cause further shear stress conditioning. Vibration of between 3 and 50 Hz is taught and 3 to 30 Hz is preferred. Higher frequencies (80 Hz and above) of body vibration have been found to be potentially harmful.

Although particular embodiments of the present invention have been shown and described, it should be understood that the above discussion is not intended to limit the present invention to these embodiments. One skilled in the art will readily appreciate that various changes and modifications may be made without departing from the spirit and scope of the present invention. Thus, the present invention is intended to cover alternatives, modifications, and equivalents that may fall within the spirit and scope of the present invention as defined by the claims.

It is understood that variations may be made in the foregoing without departing from the scope of the disclosed embodiments. Furthermore, the elements and teachings of the various illustrative embodiments may be combined in whole or in part some or all of the illustrated embodiments.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What we claim are:

1. A system for inducing physiological effects of ischemic conditioning and physiological effects of shear stress in a subject's body, the system comprising:
   (a) a first device configured to cause ischemia in a subject's body part;
   (b) a second device configured to mechanically generate arterial shear stress in a subject's body part;
   (c) a third device configured to monitor one or more of markers of ischemia or hemodynamic parameters such as tissue oxygenation and temperature; markers of metabolism including lactate, pH, oxygen, carbon dioxide, ATP, ADP, adenosine, cytochrome oxidase, redox voltage, erythropoietin, bradykinin, opioids; and markers of blood flow or pulse; or combinations thereof;
   (d) a microcontroller capable of automatically controlling a first actuator to induce ischemic condition, controlling a second actuator to control a second device to generate arterial shear stress, and controlling a third actuator to activate a third device concurrently monitoring one or more markers of ischemia or hemodynamic markers; and
   (e) a first actuator to cause the first device to cause ischemia in a subject's body part for a preset duration and then stop the ischemia for a preset duration, and to repeat the ischemia and reflow periods according to a preset program; a second actuator to simultaneously cause the second device to mechanically generate arterial shear stress according to a preset program of mechanical pulse amplitude, duration, and frequency; and a third actuator to activate the third device to concurrently monitor one or more markers of ischemia or hemodynamic parameters, wherein the microcontroller causes automatic execution of the preset programs.

2. The system of claim 1 wherein the first device utilizes one or more inflatable cuffs and the cuff is inflated to a level higher than the subject's arterial systolic pressure to occlude arterial blood flow to perform remote ischemic conditioning.

3. The system of claim 1 wherein the second device that mechanically generates arterial shear stress is comprised of one or more inflatable, pulsating cuffs.

4. The system of claim 1 wherein the second device that mechanically generates arterial shear stress is a whole or partial body vibration device.

5. The system of claim 1 comprising a group consisting of a hospital patient bed, a nursing home bed, an operating room bed, a wheelchair, an athletic performance bed, a rehabilitation bed, a rehabilitation suit, a space suit, a flight suit, a flight jacket, a vest, an armband, a pair of boots, or an orthopedic brace.

6. The system of claim 1 is part of a left ventricular assist device system.

7. The system of claim 1 wherein the monitored markers of ischemia or hemodynamic parameters are used to adjust the settings of preset programs.

8. A system for inducing physiological effects of ischemic conditioning and physiological effects of electrical stimulation in a subject's body, the system comprising:
   (a) a first device configured to cause ischemia in a subject's body part;
   (b) a second device configured to cause an electrical stimulation of one or more nerves, one or more muscles, or a combination thereof;
   (c) a third device configured to monitor one or more of markers of ischemia or hemodynamic parameters such as tissue oxygenation and temperature; markers of metabolism including lactate, pH, oxygen, carbon dioxide, ATP, ADP, adenosine, cytochrome oxidase, redox voltage, erythropoietin, bradykinin, opioids; and markers of blood flow or pulse; or combinations thereof;
   (d) a microcontroller capable of automatically controlling a first actuator to induce ischemic condition, controlling a second actuator to electrical stimulation, and controlling a third actuator to activate a third device concurrently monitoring one or more markers of ischemia or hemodynamic markers; and
   (e) a first actuator to cause the first device to cause ischemia in a subject's body part for a preset duration and then stop the ischemia for a preset duration, and to repeat the ischemia and reflow periods according to a preset program; a second actuator to simultaneously cause the second device to electrically stimulate one or more nerves, one or more muscles, or a combination thereof, according to a preset program of electrical pulse amplitude, duration, and frequency, wherein neuromodulation as well as increased metabolism of calories is achieved by the elicited muscular contractions; and a third actuator to activate the third device to concurrently monitor one or more markers of ischemia or hemodynamic markers, wherein the microcontroller causes automatic execution of the preset programs.

9. The system of claim 8 wherein the first device utilizes one or more inflatable cuffs and the cuff is inflated to a level higher than the subject's arterial systolic pressure to occlude arterial blood flow to perform remote ischemic conditioning.

10. The system of claim 8 wherein the second device utilizes one or more skin surface electrodes to deliver transcutaneous electrical stimulation to underlying peripheral nerves or muscles.

11. The system of claim 8 wherein the second device is an electromagnetic stimulator.

12. The system of claim 8 wherein the second device is comprised of one or more implantable electrodes.

13. The system of claim 8 comprising a group consisting of a hospital patient bed, a nursing home bed, an operating room bed, a wheelchair, an athletic performance bed, a rehabilitation bed, a rehabilitation suit, a space suit, a flight suit, a flight jacket, a vest, an armband, a pair of boots, or an orthopedic brace.

14. The system of claim 8 is part of a left ventricular assist device system.

15. The system of claim 8 wherein the monitored markers of ischemia or hemodynamic markers are used to adjust the settings of preset programs.

16. A system for inducing physiological effects of ischemic conditioning, physiologic effects of shear stress, and physiological effects of electrical stimulation in a subject's body, the system comprising:
   (a) a first device configured to create ischemia in a subject's body part;
   (b) a second device configured to mechanically generate arterial shear stress in a subject's body part;
   (c) a third device configured to cause an electrical stimulation of one or more nerves, one or more muscles, or a combination thereof;
   (d) a fourth device configured to monitor one or more of markers of ischemia or hemodynamic parameters such as tissue oxygenation and temperature; markers of metabolism including lactate, pH, oxygen, carbon dioxide, ATP, ADP, adenosine, cytochrome oxidase, redox voltage, erythropoietin, bradykinin, opioids; and markers of blood flow or pulse; or combinations thereof;
   (e) a microcontroller capable of automatically controlling a first actuator to induce ischemic condition, controlling a second actuator to control a second device to generate arterial shear stress, and controlling a third actuator to control electrical stimulation, and controlling a fourth actuator to activate a fourth device concurrently monitoring one or more markers of ischemia or hemodynamic markers; and
   (f) a first actuator to cause the first device to cause ischemia in a subject's body part for a preset duration and then stop the ischemia for a preset duration, and to repeat the ischemia and reflow periods according to a preset program; a second actuator to simultaneously cause the second device to mechanically generate arterial shear stress according to a preset program of mechanical pulse amplitude, duration, and frequency; a third actuator to simultaneously cause the third device to electrically stimulate a nerve or muscle, or a combination thereof, according to a preset program of electrical pulse amplitude, duration, and frequency, wherein neuromodulation as well as increased metabolism of calories is achieved by the elicited muscular contractions; a fourth actuator to activate the fourth device to concurrently monitor one or more hemodynamic markers, wherein the microcontroller causes automatic execution of the preset programs.

17. The system of claim 16 wherein the first device utilizes one or more inflatable cuffs and the cuff is inflated to a level higher than the subject's arterial systolic pressure to occlude arterial blood flow to perform remote ischemic conditioning.

18. The system of claim 16 wherein the second device that mechanically generates arterial shear stress is comprised of one or more inflatable, pulsating cuffs.

19. The system of claim 16 wherein the second device that mechanically generates arterial shear stress is a whole or partial body vibration device.

20. The system of claim 16 wherein the third device utilizes one or more skin surface electrodes to deliver transcutaneous electrical stimulation to underlying peripheral nerves or muscles.

21. The system of claim 16 wherein the third device is comprised of one or more implantable electrodes or is an electromagnetic stimulator.

22. The system of claim 16 further comprising a fifth device that provides a chemical stimulation.

23. The system of claim 16 comprising a group consisting of a hospital patient bed, a nursing home bed, an operating room bed, a wheelchair, an athletic performance bed, a rehabilitation bed, a rehabilitation suit, a space suit, a flight suit, a flight jacket, a vest, an armband, a pair of boots, or an orthopedic brace.

24. The system of claim 16 is part of a left ventricular assist device system.

25. The system of claim 16 wherein the monitored markers of ischemia or hemodynamic markers are used to adjust the settings of preset programs.

* * * * *